(12) United States Patent
DiLorenzo

(10) Patent No.: US 7,529,582 B1
(45) Date of Patent: May 5, 2009

(54) METHOD AND APPARATUS FOR NEUROMODULATION AND PHYSIOLOGIC MODULATION FOR THE TREATMENT OF METABOLIC AND NEUROPSYCHIATRIC DISEASE

(75) Inventor: Daniel John DiLorenzo, New Orleans, LA (US)

(73) Assignee: DiLorenzo Biomedical, LLC, Seattle, WA (US)

( * ) Notice: Subject to any disclaimer, the term of this patent is extended or adjusted under 35 U.S.C. 154(b) by 118 days.

(21) Appl. No.: 10/872,549

(22) Filed: Jun. 21, 2004

Related U.S. Application Data

(63) Continuation of application No. 10/198,871, filed on Jul. 19, 2002, and a continuation of application No. 10/008,576, filed on Nov. 11, 2001, now Pat. No. 6,819,956, which is a continuation of application No. 09/340,326, filed on Jun. 25, 1999, now Pat. No. 6,366,813, application No. 10/872,549, which is a continuation of application No. 10/718,248, filed on Nov. 20, 2003, application No. 10/872,549, which is a continuation of application No. 10/753,205, filed on Jan. 6, 2004, application No. 10/872,549, which is a continuation of application No. 10/818,333, filed on Apr. 5, 2004.

(60) Provisional application No. 60/579,074, filed on Jun. 10, 2004, provisional application No. 60/500,911, filed on Sep. 5, 2003, provisional application No. 60/460,140, filed on Apr. 3, 2003, provisional application No. 60/438,286, filed on Jan. 6, 2003, provisional application No. 60/436,792, filed on Dec. 27, 2002, provisional application No. 60/427,699, filed on Nov. 20, 2002, provisional application No. 60/307,124, filed on Jul. 23, 2001, provisional application No. 60/095,413, filed on Aug. 5, 1998.

(51) Int. Cl.
*A61N 1/18* (2006.01)
(52) U.S. Cl. .......................................................... 607/2
(58) Field of Classification Search ...................... None
See application file for complete search history.

(56) References Cited

U.S. PATENT DOCUMENTS

| 6,246,912 B1 * | 6/2001 | Sluijter et al. ............... 607/100 |
| 6,266,564 B1 * | 7/2001 | Hill et al. ........................ 607/9 |
| 6,862,479 B1 * | 3/2005 | Whitehurst et al. ........... 607/39 |

(Continued)

OTHER PUBLICATIONS

Felton, D.L. and R.F. Jozefowicz, "Netter's Atlas of Human Neuroscience", Icon Learning Systems, Teterboro, NJ, 2004, p. 126.

(Continued)

*Primary Examiner*—Carl H Layno
*Assistant Examiner*—Yun Haeng Lee
(74) *Attorney, Agent, or Firm*—Daniel John DiLorenzo; Ryan Kromholz & Manion, SC

(57) ABSTRACT

A method and apparatus for physiological modulation, including neural and gastrointestinal modulation, for the purposes of treating several disorders, including obesity, depression, epilepsy, and diabetes. This includes chronically implanted neural and neuromuscular modulators, used to modulate the afferent neurons of the sympathetic nervous system to induce satiety. Furthermore, this includes neuromuscular stimulation of the stomach to effect baseline and intermittent smooth muscle contraction to increase gastric intraluminal pressure, which induces satiety, and stimulate sympathetic afferent fibers, including those in the sympathetic trunk, splanchnic nerves, and greater curvature of the stomach, to augment the perception of satiety.

234 Claims, 18 Drawing Sheets

U.S. PATENT DOCUMENTS

| | | |
|---|---|---|
| 2003/0018367 A1 | 1/2003 | DiLorenzo |
| 2003/0181958 A1 | 9/2003 | Dobak, III |
| 2003/0181959 A1 | 9/2003 | Dobak, III |
| 2004/0162594 A1* | 8/2004 | King .......................... 607/40 |
| 2006/0116736 A1* | 6/2006 | DiLorenzo ................... 607/40 |
| 2006/0167498 A1* | 7/2006 | DiLorenzo .................... 607/2 |

OTHER PUBLICATIONS

Daniel et al., "Criteria for Differentiation of Brown and White Fat in the Rat", Canadian Journal of Physiology and Pharmacology, vol. 47, 1969; pp. 941-945.

Zardetto-Smith et al., "Catecholamine and NPY Efferents From the Ventrolateral Medulla to the Amygdala in the Rat",Brain Research Bulletin, vol. 38, No. 3, 1995, pp. 253-260.

Barone et al., "Gastric Distension Modulates Hypothalamic Neurons Via a Sympathetic Afferent Path Through the Mesencephalic Periaqueductal Gray", Brain Research Bulletin, vol. 38, No. 3, 1995; pp. 239-251.

Ban, Tadayasu; "Fiber Connections in the Hypothalamus and Some Autonomic Functions", Central Neural Control of Eating and Obesity, Pharmacology Biochemistry and Behavior, vol. 3, Suppl. 1; 1975, pp. 3-13.

Brown et al., "Changes in Food Intake with Electrical Stimulation of the Ventromedial Hypothalamus in Dogs", Journal of Neurosurgery, vol. 60, 1984, pp. 1253-1257.

Derry et al., "Two Sympathetic Nerve Supplies to Brown Adipose Tissue of the Rat", Canadian Journal of Physiology and Pharmacology, vol. 47, 1969, pp. 57-63.

Flaim et al., "Coupling of Signals to Brown Fat: $\alpha$-and $\beta$-Adrenergic Responses in Intact Rats", In Vivo Adrenergic Responses of Brown Adipose Tissue, 1976, pp. R101-R109.

Takahashi et al., "Hypothalamic Regulation of Lipid Metabolism in the Rat: Effect of Hypothalamic Stimulation on Lipogenesis", Journal of the Autonomic Nervous System, vol. 6, 1984, pp. 225-235.

Yuan et al, "Hypothalamic Unitary Responses to Gastric Vagal Input from the Proximal Stomach", Gastric Vagal Input to Hypothalamus, 1992, pp. G74-G80.

Astrup A, Breum L. Toubro S, Hein P, Quaade F. The effect and safety of an ephedrine/caffeine compound compared to ephedrine, caffeine and placebo in obese subjects on an energy restricted diet. A double blind trial. Int.J.Obes.Relat Metab Disord. (1992), pp. 269-277.

Astrup A, Buemann B, Christensen NJ, Toubro S, Thorbek G, Victor OJ, Quaade F. The effect of ephedrine/caffeine mixture on energy expenditure and body composition in obese women. Metabolism (1992), pp. 686-688.

Astrup A, Toubro S, Christensen NJ, Quaade F. Pharmacology of thermogenic drugs. Am.J.Clin.Nutr. (1992), pp. 246S-248S.

Babinski M. Tumeur du corps pituitaire sans acromegalie et avec arret de developpement des organes genitaux. Rev Neurol (1900), pp. 531-533.

Berthoud HR, Niijima A, Sauter JF, Jeanrenaud B. Evidence for a role of the gastric, coeliac and hepatic branches in vagally stimulated insulin secretion in the rat. J.Auton.Nerv.Syst. (1983), pp. 97-110.

Bray GA. Obesity, a disorder of nutrient partitioning: the Mona Lisa hypothesis. J.Nutr. (1991), pp. 1146-1162.

Bray GA. Genetic, hypothalamic and endocrine features of clinical and experimental obesity. Prog.Brain Res. (1992), pp. 333-340.

Bray GA. Reciprocal relation of food intake and sympathetic activity: experimental observations and clinical implications. Int.J. Obes. Relat Metab Disord. (2000), pp. S8-17.

Bray GA, Gallagher TF, Jr. Manifestations of hypothalamic obesity in man: a comprehensive investigation of eight patients and a review of the literature. Medicine (Baltimore) (1975), pp. 301-330.

Bray GA, York DA, Fisler JS. Experimental obesity: a homeostatic failure due to defective nutrient stimulation of the sympathetic nervous system. Vitam.Horm. (1989), pp. 1-125.

Bruch H. The Frohlich syndrome: report of the original case. 1939. Obes. Res. (1939), pp. 329-331.

Cigaina V, V, Saggioro A, Rigo V, V, Pinato G, Ischai S. Long-term Effects of Gastric Pacing to Reduce Feed Intake in Swine. Obes.Surg. (1996), pp. 250-253.

Dulloo AG. Ephedrine, xanthines and prostaglandin-inhibitors: actions and interactions in the stimulation of thermogenesis. Int.J. Obes.Relat Metab Disord. (1993), pp. S35-S40.

Greenway FL. The safety and efficacy of pharmaceutical and herbal caffeine and ephedrine use as a weight loss agent. Obes.Rev. (2001), pp. 199-211.

Inoue S, Bray GA. The effects of subdiaphragmatic vagotomy in rats with ventromedial hypothalamic obesity. Endocrinology (1977), pp. 108-114.

Inoue S, Bray GA, Mullen YS. Transplantation of pancreatic beta-cells prevents development of hypothalamic obesity in rats. Am.J. Physiol (1978), pp. E266-E271.

Jeanrenaud B. Energy fuel and hormonal profile in experimental obesities. Experientia Suppl (1983), pp. 57-76.

King BM, Frohman LA. The role of vagally-medicated hyperinsulinemia in hypothalamic obesity. Neurosci.Biobehav.Rev. (1982), pp. 205-214. [28] Kral JG. Vagotomy.

Niijima A, Rohner-Jeanrenaud F, Jeanrenaud B. Role of ventromedial hypothalamus on sympathetic efferents of brown adipose tissue. Am.J.Physiol (1984), pp. R650-R654.

Pasquali R, Casimirri F, Melchionda N, Grossi G, Bortoluzzi L, Morselli Labate AM, Stefanini C, Raltano A. Effects of chronic administration of ephedrine during very-low calorie diets on energy expenditure, protein metabolism and hormone levels in obese subjects. Clin.Sci.(Lond) (1992), pp. 85-92.

Perkins MN, Rothwell NJ, Stock MJ, Stone TW. Activation of brown adipose tissue thermogenesis by the ventromedial hypothalamus. Nature (1981), pp. 401-402.

Pories WJ, Swanson MS, MacDonald KG, Long SB, Morris PG, Brown BM, Barakat HA, deRamon RA, Israel G, Dolezal JM, . Who would have thought it? An operation proves to be the most effective therapy for adult-onset diabetes mellitus. Ann.Surg. (1995), pp. 339-350.

Reeves AG, Plum F. Hyperphagia, rage, and dementia accompanying a ventromedial hypothalamic neoplasm. Arch. Neurol. (1969), pp. 616-624.

Sakaguchi T, Bray GA, Eddlestone G. Sympathetic activity following paraventricular or ventromedial hypothalamic lesions in rats. Brain Res.Bull. (1988), pp. 461-465.

Sauter JF, Berthoud HR, Jeanrenaud B. A simple electrode for intact nerve stimulation and/or recording in semi-chronic rats. Pflugers Arch. (1983), pp. 68-69.

Seydoux J, ssimacopoulos-Jeannet F, Jeanrenaud B. Girardier L. Alterations of brown adipose tissue in genetically obese (ob/ob) mice. I. Demonstration of loss of metabolic response to nerve stimulation and catecholamines and its partial recovery after fasting or cold adaptation. Endocrinology (1982), pp. 432-438.

Shimizu H, Shargill NS, Bray GA. Adrenalectomy and response to corticosterone and MSH in the genetically obese yellow mouse. Am.J.Physiol (1989), pp. R494-R500. [38] Smith DK, Sarfeh J, Howard L. Truncal vagotomy.

Tokunaga K, Fukushima M, Kemnitz JW, Bray GA. Effect of vagotomy on serum insulin in rats with paraventricular or ventromedial hypothalamic lesions. Endocrinology (1986), pp. 1708-1711. [40] Vander Tuig JG, Knehans AW, Romsos DR. Reduced sympathetic nervous system activity in rats with ventromedial hypothalamic lesions. Life Sci. (1982), pp. 913-920.

York DA, Bray GA. Dependence of hypothalamic obesity on insulin, the pituitary and the adrenal gland. Endocrinology (1972), pp. 885-894.

Yoshida T, Bray GA. Catecholamine turnover in rats with ventromedial hypothalamic lesions. Am.J.Physiol (1984), pp. R558-R565.

* cited by examiner

METHOD AND APPARATUS FOR NEUROMODULATION AND PHYSIOLOGIC MODULATION FOR THE TREATMENT OF METABOLIC AND NEUROPSYCHIATRIC DISEASE

CROSS REFERENCE TO RELATED APPLICATIONS

This application is a continuation of U.S. patent application Ser. No. 10/198,871, entitled METHOD AND APPARATUS FOR NEUROMODULATION AND PHYSIOLOGIC MODULATION FOR THE TREATMENT OF METABOLIC AND NEUROPSYCHIATRIC DISEASE, filed Jul. 19, 2002, and naming as inventor Daniel John DiLorenzo, which claims the benefit of U.S. Provisional Patent Application Ser. No. 60/307,124, entitled PHYSIOLOGIC MODULATION FOR THE CONTROL OF OBESITY, DEPRESSION, EPILEPSY, AND DIABETES, filed Jul. 19, 2001, and naming as inventor Daniel John DiLorenzo.

This application claims the benefit of U.S. Provisional Patent Application No. 60/500,911, filed Sep. 5, 2003 and naming as inventor Daniel John DiLorenzo.

This application also claims the benefit of U.S. Provisional Patent Application No. 60/579,074, filed Jun. 10, 2004 and naming as inventor Daniel John DiLorenzo.

This application claims the benefit of U.S. patent application Ser. No. 10/008,576, entitled OPTIMAL METHOD AND APPARATUS FOR NEURAL MODULATION FOR THE TREATMENT OF NEUROLOGICAL DISEASE, PARTICULARLY MOVEMENT DISORDERS, filed Nov. 11, 2001, and naming as inventor Daniel John DiLorenzo; which is a continuation of U.S. patent application Ser. No. 09/340,326, entitled APPARATUS AND METHOD FOR CLOSED-LOOP INTRACRANIAL STIMULATION FOR OPTIMAL CONTROL OF NEUROLOGICAL DISEASE, filed Jun. 25, 1999, and naming as inventor Daniel John DiLorenzo; which claims the benefit of U.S. Provisional Patent Application Ser. No. 60/095,413 entitled OPTIMAL METHOD AND APPARATUS FOR NEURAL MODULATION FOR THE TREATMENT OF NEUROLOGICAL DISEASE, PARTICULARLY MOVEMENT DISORDERS, filed Aug. 5, 1998 and naming as inventor Daniel John DiLorenzo.

This application also claims the benefit of prior, U.S. Provisional Application Ser. No. 60/427,699, entitled APPARATUS AND METHOD FOR CLOSED-LOOP INTRACRANIAL SIMULATION FOR OPTIMAL CONTROL OF NEUROLOGICAL DISEASE, filed Nov. 20, 2002, and naming as inventor Daniel John DiLorenzo.

This application also claims the benefit of prior, U.S. Provisional Application Ser. No. 60/436,792, entitled APPARATUS AND METHOD FOR CLOSED-LOOP INTRACRANIAL STIMULATION FOR OPTIMAL CONTROL OF NEUROLOGICAL DISEASE, filed Dec. 27, 2002, and naming as inventor Daniel John DiLorenzo.

This application also claims the benefit of prior, now abandoned U.S. Provisional Application Ser. No. 60/438,286, entitled ADAPTIVE CLOSED-LOOP NEUROMODULATION SYSTEM, filed Jan. 6, 2003, and naming as inventor Daniel John DiLorenzo.

This application also claims the benefit of prior, now abandoned (under 35 U.S.C. 119(e)(3)) U.S. Provisional Application Ser. No. 60/460,140 filed Apr. 3, 2003.

BACKGROUND OF INVENTION

1. Field of the Invention

The present invention relates generally to metabolic disease and neuropsychiatric disease and, more particularly, to stimulation of gastric and sympathetic neural tissue for the treatment of obesity and depression.

2. Related Art

Physiologic studies have demonstrated the presence of a sympathetic nervous system afferent pathway transmitting gastric distension information to the hypothalamus. [Barone, Zarco de Coronado et al. (1995). Gastric distension modulates hypothalamic neurons via a sympathetic afferent path through the mesencephalic periaqueductal gray. Brain Research Bulletin. 38: 239-51.] However, prior techniques have generally not addressed the problems associated with satiety, morbidity, mortality of intracranial modulation and the risk of ulcers. Unlike prior techniques, by specifically targeting sympathetic afferent fibers, the present invention effects the sensation of satiety and avoids the substantial risks of morbidity and mortality of intracranial modulation, particularly dangerous in the vicinity of the hypothalamus. Furthermore, this invention avoids the risk of ulcers inherent in vagus nerve stimulation.

A. Satiety

Stimulation of intracranial structures has been proposed and described for the treatment of obesity (U.S. Pat. No. 5,782,798). Stimulation of the left ventromedial hypothalamic (VMH) nucleus resulted in delayed eating by dogs who had been food deprived. Following 24 hours of food deprivation, dogs with VMH stimulation waited between 1 and 18 hours after food presentation before consuming a meal. Sham control dogs ate immediately upon food presentation. Dogs that received 1 hour of stimulation every 12 hours for 3 consecutive days maintained an average daily food intake of 35% of normal baseline levels. [Brown, Fessler et al. (1984). Changes in food intake with electrical stimulation of the ventromedial hypothalamus in dogs. Journal of Neurosurgery. 60: 1253-7.]

B. Candidate Peripheral Nerve Pathways for Modulating Satiety

B1. Sympathetic Afferents

The effect of gastric distension on activity in the lateral hypothalamus-lateral preoptic area-medical forebrain bundle (LPA-LH-MFB) was studied to determine the pathways for this gastric afferent input to the hypothalamus. [Barone, Zarco de Coronado et al. (1995). Gastric distension modulates hypothalamic neurons via a sympathetic afferent path through the mesencephalic periaqueductal gray. Brain Research Bulletin. 38: 239-51.] The periaqueductal gray matter (PAG) was found to be a relay station for this information. [Barone, Zarco de Coronado et al. (1995). Gastric distension modulates hypothalamic neurons via a sympathetic afferent path through the mesencephalic periaqueductal gray. Brain Research Bulletin. 38: 239-51.] This modulation of the hypothalamus was attenuated but not permanently eliminated by bilateral transection of the vagus nerve. This modulation was, however, significantly reduced or eliminated by bilateral transection of the cervical sympathetic chain or spinal transection at the first cervical level. [Barone, Zarco de Coronado et al. (1995). Gastric distension modulates hypothalamic neurons via a sympathetic afferent path through the mesencephalic periaqueductal gray. Brain Research Bulletin. 38: 239-51.] These signals containing gastric distension and temperature stimulation are mediated to a large degree by sympathetic afferents, and the PAG is a relay station for this gastric afferent input to the hypothalamus. [Barone, Zarco de Coronado et al. (1995). Gastric distension modulates hypothalamic neurons via a sympathetic afferent path through the mesencephalic periaqueductal gray. Brain Research Bulletin. 38: 239-51.] For example, in the LPA-LH-MFB study, 26.1% of the 245 neurons studied were affected by gastric stimulation, with 17.6% increasing in firing frequency and 8.6% decreasing during gastric distension. [Barone, Zarco de Coronado et al. (1995). Gastric distension modulates hypothalamic neurons via a sympathetic afferent path through the mesencephalic periaqueductal gray. Brain Research Bulletin. 38: 239-51.] The response of 8 of 8 neurons sensitive to gastric distension were maintained, though attenuated after bilateral vagus nerves were cut. In 2 of these 8 cells, the effect was transiently eliminated for 2-4 minutes after left vagus transection, and then activity recovered. In 3 LH-MFB cells, two increased and the other decreased firing rate with gastric distension. Following bilateral sympathetic ganglion transection, the response of two were eliminated, and the third (which increased firing with distension) had a significantly attenuated response. [Barone, Zarco de Coronado et al. (1995). Gastric distension modulates hypothalamic neurons via a sympathetic afferent path through the mesencephalic periaqueductal gray. Brain Research Bulletin. 38: 239-51.] Vagus stimulation resulted in opposite or similar responses as gastric distension on the mesencephalic cells.

B2. Vagus Nerve Afferents

Gastric vagus input to neurons throughout the hypothalamus has been characterized. [Yuan and Barber (1992). Hypothalamic unitary responses to gastric vagal input from the proximal stomach. American Journal of Physiology. 262: G74-80.] Nonselective epineural vagus nerve stimulation (VNS) has been described for the treatment of Obesity (U.S. Pat. No. 5,188,104). This suffers from several significant limitations that are overcome by the present invention.

The vagus nerve is well known to mediate gastric hydrochloric acid secretion. Dissection of the vagus nerve off the stomach is often performed as part of major gastric surgery for ulcers. Stimulation of the vagus nerve may pose risks for ulcers in patients, of particular concern, as obese patients often have gastroesophageal reflux disease (GERD); further augmentation of gastric acid secretion would only exacerbate this condition.

C. Assessment of Sympathetic and Vagus Stimulation

The present invention teaches a significantly more advanced neuroelectric interface technology to stimulate the vagus nerve and avoid the efferent vagus side effects, including speech and cardiac side effects common in with existing VNS technology as well as the potential ulcerogenic side effects. However, since sympathetic afferent activity appears more responsive to gastric distension, this may represent a stronger channel for modulating satiety. Furthermore, by pacing stimulating modulators on the greater curvature of the stomach, one may stimulate the majority of the circular layer of gastric musculature, thereby diffusely increasing gastric tone.

D. Neuromuscular Stimulation

The muscular layer of the stomach is comprised of 3 layers: (1) an outer longitudinal layer, (2) a circular layer in between, and (3) a deeper oblique layer. [Gray (1974). Gray's Anatomy. T. Pick and R. Howden. Philadelphia, Running Press.] The circular fibers, which lie deep to the superficial longitudinal fibers, would appear to be the layer of choice for creating uniform and consistent gastric contraction with elevated wall tension and luminal pressure. Therefore, modulators should have the ability to deliver stimulation through the longitudinal layer. If the modulator is in the form of an electrode, then the electrodes should have the ability to deliver current through the longitudinal layer.

Gray's Anatomy describes innervation as including the right and left pneumogastric nerves (not the vagus nerves), being distributed on the back and front of the stomach, respectively. A great number of branches from the sympathetic nervous system also supply the stomach. [Gray (1974). Gray's Anatomy. T. Pick and R. Howden. Philadelphia, Running Press.] Metabolic Modulation (Efferent) Electrical stimulation of the VMH enhances lipogenesis in the brown adipose tissue (BAT), preferentially over the white adipose tissue (WAT) and liver, probably through a mechanism involving activation of the sympathetic innervation of the BAT. [Takahashi and Shimazu (1982). Hypothalamic regulation of lipid metabolism in the rat: effect of hypothalamic stimulation on lipogenesis. Journal of the Autonomic Nervous System. 6: 225-35.] The VMH is a hypothalamic component of the sympathetic nervous system. [Ban (1975). Fiber connections in the hypothalamus and some autonomic functions. Pharmacology, Biochemistry & Behavior. 3: 3-13.] A thermogenic response in BAT was observed with direct sympathetic nerve stimulation. [Flaim, Horwitz et al. (1977). Coupling of signals to brown fat: a- and b-adrenergic responses in intact rats. Amer. J. Physiol. 232: R101-R109.] The BAT had abundant sympathetic innervation with adrenergic fibers that form nest-like networks around every fat cell, [Derry, Schonabum et al. (1969). Two sympathetic nerve supplies to brown adipose tissue of the rat. Canad. J. Physiol. Pharmacol. 47: 57-63.] whereas WAT has no adrenergic fibers in direct contact with fat cells except those related to the blood vessels. [Daniel and Derry (1969). Criteria for differentiation of brown and white fat in the rat. Canad. J. Physiol. Pharmacol. 47: 941-945.]

SUMMARY OF INVENTION

The present invention teaches apparatus and methods for treating a multiplicity of diseases, including obesity, depression, epilepsy, diabetes, and other diseases. The invention taught herein employs a variety of energy modalities to modulate central nervous system structures, peripheral nervous system structures, and peripheral tissues and to modulate physiology of neural structures and other organs, including gastrointestinal, adipose, pancreatic, and other tissues. The methods for performing this modulation, including the sites of stimulation and the modulator configurations are described. The apparatus for performing the stimulation are also described. This invention teaches a combination of novel anatomic approaches and apparatus designs for direct and indirect modulation of the autonomic nervous system, which is comprised of the sympathetic nervous system and the parasympathetic nervous system.

For the purposes of this description the term GastroPace should be interpreted to mean the devices constituting the system of the present embodiment of this invention.

A. Obesity and Eating Disorders

The present invention teaches several mechanisms, including neural modulation and direct contraction of the gastric musculature, to effect the perception of satiety. This modulation is useful in the treatment of obesity and eating disorders, including anorexia nervosa and bulemia.

Direct stimulation of the gastric musculature increases the intraluminal pressure within the stomach; and this simulates the physiologic condition of having a full stomach, sensed by stretch receptors in the muscle tissue and transmitted via neural afferent pathways to the hypothalamus and other central nervous system structures, where the neural activity is perceived as satiety.

This may be accomplished with the several alternative devices and methods taught in the present invention. Stimulation of any of the gastric fundus, greater curvature of stomach, pyloric antrum, or lesser curvature of stomach, or other region of the stomach or gastrointestinal tract, increases the intraluminal pressure. Increase of intraluminal pressure physiologically resembles fullness of the respective organ, and satiety is perceived.

The present invention also includes the restriction of the flow of food to effect satiety. This is accomplished by stimulation of the pylorous. The pylorus is the sphincter-like muscle at the distal juncture of the stomach with the duodenum, and it regulates food outflow from the stomach into the duodenum. By stimulating contraction of the pylorus, food outflow from the stomach is slowed or delayed. The presence of a volume of food in the stomach distends the gastric musculature and causes the person to experience satiety.

B. Depression and Anxiety

An association has been made between depression and overeating, particularly with the craving of carbohydrates; and is believed to be an association between the sense of satiety and relief of depression. Stimulation of the gastric tissues, in a manner that resembles or is perceived as satiety, as described above, provides relief from this craving and thereby relief from some depressive symptoms.

There are several mechanisms, including those taught above for the treatment of obesity that are applicable to the treatment of depression, anxiety, and other neuropsychiatric conditions.

C. Epilepsy

The present invention includes electrical stimulation of peripheral nervous system and other structures and tissues to modulate the activity in the central nervous system to control seizure activity.

This modulation takes the form of peripheral nervous system stimulation using a multiplicity of novel techniques and apparatus. Direct stimulation of peripheral nerves is taught; this includes stimulation of the vagus, trigeminal, accessory, and sympathetic nerves. Indiscriminate stimulation of the vagus nerves has been described for some disorders, but the limitations in this technique are substantial, including cardiac rhythm disruptions, speech difficulties, and gastric and duodenal ulcers. The present invention overcomes these persistent limitations by teaching a method and apparatus for the selective stimulation of structures, including the vagus nerve as well as other peripheral nerves, and other neural, neuromuscular, and other tissues.

The present invention further includes noninvasive techniques for neural modulation. This includes the use of tactile stimulation to activate peripheral or cranial nerves. This noninvasive stimulation includes the use of tactile stimulation, including light touch, pressure, vibration, and other modalities that may be used to activate the peripheral or cranial nerves. Temperature stimulation, including hot and cold, as well as constant or variable temperatures, are included in the present invention.

D. Diabetes

The response of the gastrointestinal system, including the pancreas, to a meal includes several phases. The first phase, the anticipatory stage, is neurally mediated. Prior to the actual consumption of a meal, saliva production increases and the gastrointestinal system prepares for the digestion of the food to be ingested. Innervation of the pancreas, in an analogous manner, controls production of insulin.

Modulation of pancreatic production of insulin may be performed by modulation of at least one of afferent or efferent neural structures. Afferent modulation of at least one of the vagus nerve, the sympathetic structures innervating the gastrointestinal tissue, the sympathetic trunk, and the gastrointestinal tissues themselves is used as an input signal to influence central and peripheral nervous system control of insulin secretion.

DETAILED DESCRIPTION

Figure 1:
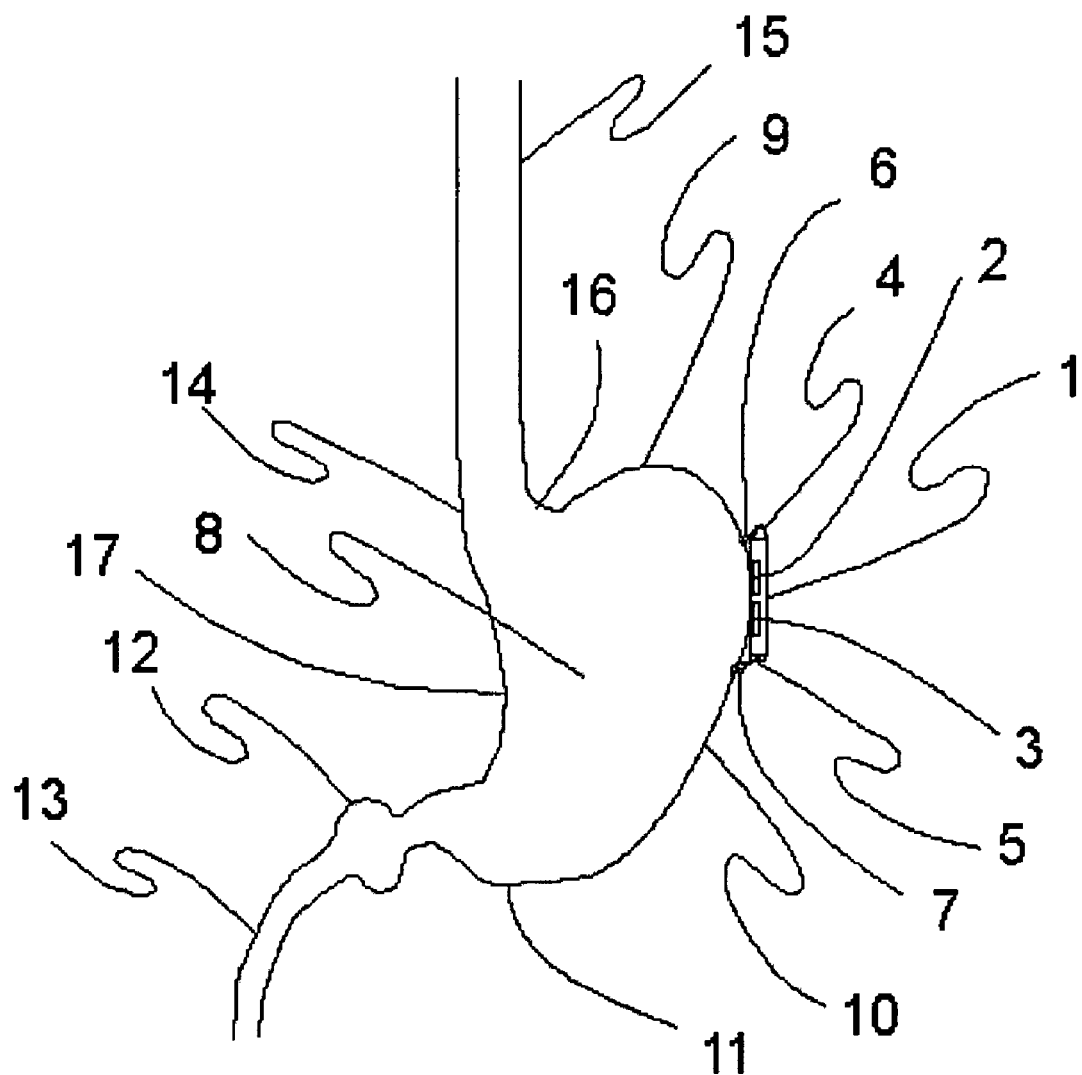
FIG. 1 depicts GastroPace implanted along the Superior Greater Curvature of the stomach for both Neural Afferent and Neuromuscular Modulation.

The present invention encompasses a multimodality technique, method, and apparatus for the treatment of several diseases, including but not limited to obesity, eating disorders, depression, epilepsy, and diabetes.

These modalities may be used for diagnostic and therapeutic uses, and these modalities include but are not limited to stimulation of gastric tissue, stimulation of gastric musculature, stimulation of gastric neural tissue, stimulation of sympathetic nervous tissue, stimulation of parasympathetic nervous tissue, stimulation of peripheral nervous tissue, stimulation of central nervous tissue, stimulation of cranial nervous tissue, stimulation of skin receptors, including Pacinian corpuscles, nociceptors, golgi tendons, and other sensory tissues in the skin, subcutaneous tissue, muscles, and joints.

Stimulation may be accomplished by electrical means, optical means, electromagnetic means, radiofrequency means, electrostatic means, magnetic means, vibrotactile means, pressure means, pharmacologic means, chemical means, electrolytic concentration means, thermal means, or other means for altering tissue activity.

Already encompassed in the above description are several specific applications of this broad technology. These specific applications include electrical stimulation of gastric tissue, including at least one of muscle and neural, for the control of appetite and satiety, and for the treatment of obesity. Additional specific uses include electrical stimulation of gastric tissue for the treatment of depression. Further uses include electrical stimulation of pancreatic tissue for the treatment of diabetes.

A. Satiety Modulation

A1. Sympathetic Afferent Stimulation

Selected stimulation of the sympathetic nervous system is an objective of the present invention. A variety of modulator designs and configurations are included in the present invention and other designs and configurations may be apparent to those skilled in the art and these are also included in the present invention. Said modulator may take the form of electrode or electrical source, optical source, electromagnetic source, radiofrequency source, electrostatic source, magnetic source, vibrotactile source, pressure source, pharmacologic source, chemical source, electrolyte source, thermal source, or other energy or stimulus source.

One objective of the modulator design for selective sympathetic nervous system stimulation is the avoidance of stimulation of the vagus nerve. Stimulation of the vagus nerve poses the risk enhanced propensity for development of gastric or duodenal ulcers.

Other techniques in which electrical stimulation has been used for the treatment of obesity have included stimulation of central nervous system structures or peripheral nervous system structures. Other techniques have used sequential stimulation of the gastric tissue to interrupt peristalsis; however, this broad stimulation of gastric tissue necessarily overlaps regions heavily innervated by the vagus nerve and consequently poses the same risks of gastric and duodenal ulcers that stimulation of the vagus nerve does.

One objective of the present invention is the selective stimulation of said afferent neural fibers that innervate gastric tissue. Avoidance of vagus nerve stimulation is an object of this modulator configuration. Other alternative approaches to gastric pacing involving gastric muscle stimulation secondarily cause stimulation of the vagus nerve as well as stimulation of gastric tissues in acid-secreting regions, consequently posting the undesirable side effects of gastric and duodenal ulcers secondary to activation of gastric acid stimulation.

There are a number of approaches to selective stimulation of the sympathetic nervous system. This invention includes stimulation of the sympathetic fibers at sites including the zones of innervation of the stomach, the gastric innervation zones excluding those innervated by vagus branches, the distal sympathetic branches proximal to the stomach, the sympathetic trunk, the intermediolateral nucleus, the locus ceruleus, the hypothalamus, and other structures comprising or influencing sympathetic afferent activity.

Stimulation of the sympathetic afferent fibers elicits the perception of satiety, and achievement of chronic, safe, and efficacious modulation of sympathetic afferents is one of the major objectives of the present invention.

Alternating and augmenting stimulation of the sympathetic nervous system and vagus nerve is included in the present invention. By alternating stimulation of the vagus nerve and the sympathetic afferent fibers, one may induce the sensation of satiety in the implanted patient while minimizing the potential risks for gastric and duodenal ulcers.

Since vagus and sympathetic afferent fibers carry information that is related to gastric distension, a major objective of the present invention is the optimization stimulation of the biggest fibers, the afferent sympathetic nervous system fibers, and other afferent pathways such that a maximal sensation of satiety is perceived in the implanted individual and such that habituation of this sensation of satiety is minimized. This optimization is performed in any combination of matters including temporal patterning of the individual signals to each neural pathway, including but not limited to the vagus nerve and sympathetic afferents, as well as temporal patterning between a multiplicity of stimulation channels involving the same were neural pathways. The present invention teaches a multiplicity of apparatus and method for stimulation of afferent sympathetic fibers, as detailed below. Other techniques and apparatus may become apparent to those skilled in the art, without departing from the present invention.

A1a. Sympathetic Afferents—Gastric Region

Figure 2:
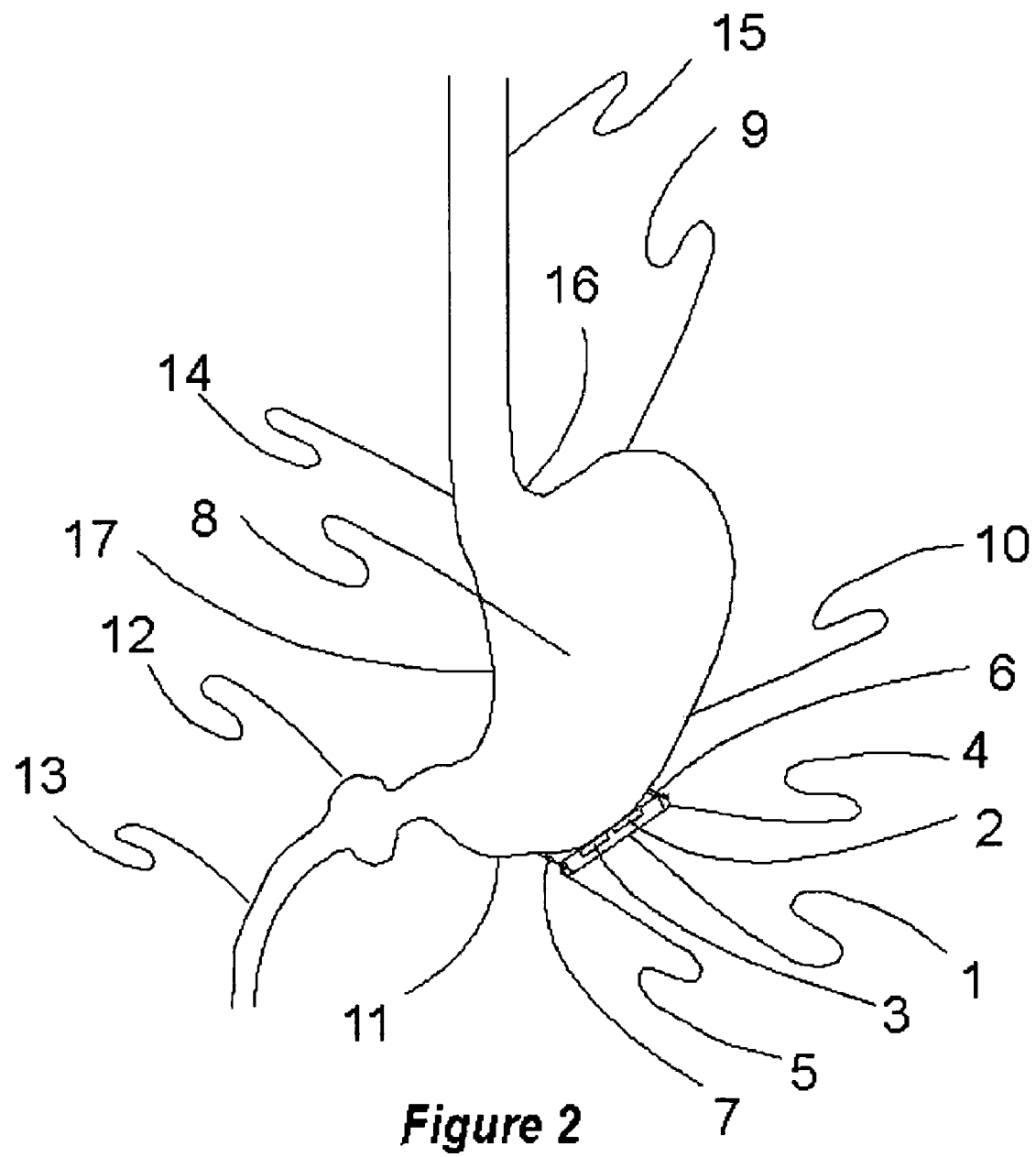
FIG. 2 depicts GastroPace implanted along the Inferior Greater Curvature of the stomach for both Neural Afferent and Neuromuscular Modulation.
Figure 3:
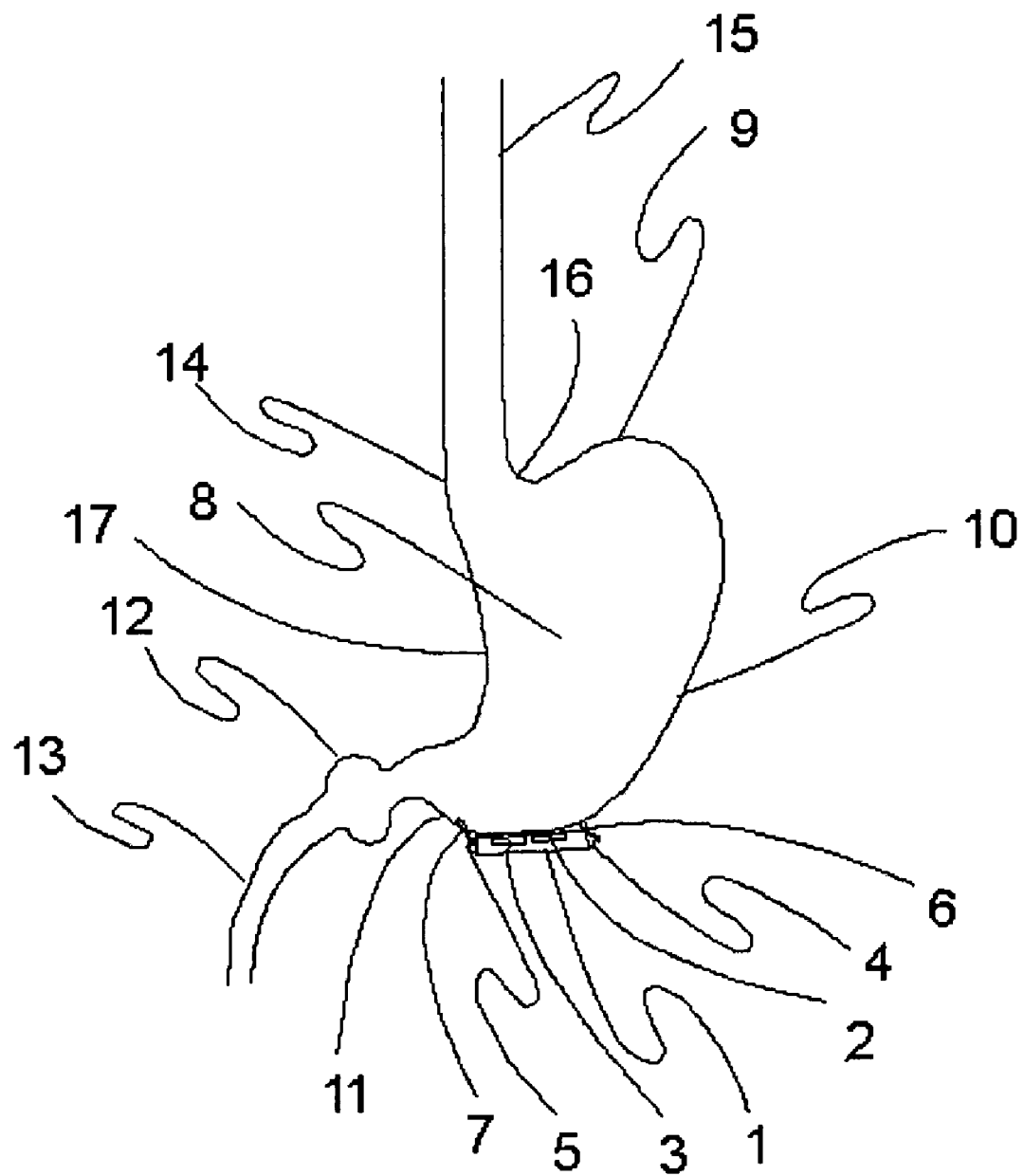
FIG. 3 depicts GastoPace implanted along the Pyloric Antrum of the stomach for both Neural Afferent and Neuromuscular Modulation.

FIG. 1 through FIG. 3 demonstrate stimulation of gastric tissue, including at least one of neural and muscular tissue. Anatomical structures include esophagus 15, lower esophageal sphincter 14, stomach 8, cardiac notch of stomach 16, gastric fundus 9, grater curvature of stomach 10, pyloric antrum 11, lesser curvature of stomach 17, pylorus 12, and duodenum 13.

Implantable pulse generator 1 is shown with modulator 2 and modulator 3 in contact with the corresponding portion of stomach 8 in the respective figures, detailed below. Implantable pulse generator further comprises attachment fixture 4 and attachment fixture 5. Additional or fewer attachment fixtures may be included without departing from the present invention. Attachment means 6 and attachment means 7 are used to secure attachment fixture 4 and attachment fixture 5, respectively to appropriate portion of stomach 8. Attachment means 6 and attachment means 7 may be comprised from surgical suture material, surgical staples, adhesives, or other means without departing from the present invention.

FIGS. 1, 2, and 3 show implantable pulse generator 1 in several anatomical positions. In FIG. 1, Implantable pulse generator 1 is shown positioned along the superior region of the greater curvature of stomach 10, with modulator 2 and modulator 3 in contact with the tissues comprising the greater curvature of stomach 10. In FIG. 2, implantable pulse generator 1 is shown positioned along the inferior region of the greater curvature of stomach 10, with modulator 2 and modulator 3 in contact with the tissues comprising the greater curvature of stomach 10. In FIG. 3, implantable pulse generator 1 is shown positioned along the pyloric antrum 11, with modulator 2 and modulator 3 in contact with the tissues comprising the pyloric antrum 11.

Modulator 2 and modulator 3 are used to stimulate at least one of gastric longitudinal muscle layer, gastric circular muscle layer, gastric nervous tissue, or other tissue. Modulator 2 and modulator 3 may be fabricated from nonpenetrating material or from penetrating material, including needed tips, arrays of needle tips, wires, conductive sutures, other conductive material, or other material, without departing from the present invention.

A1b. Sympathetic Afferents—Sympathetic Trunk

Figure 14:
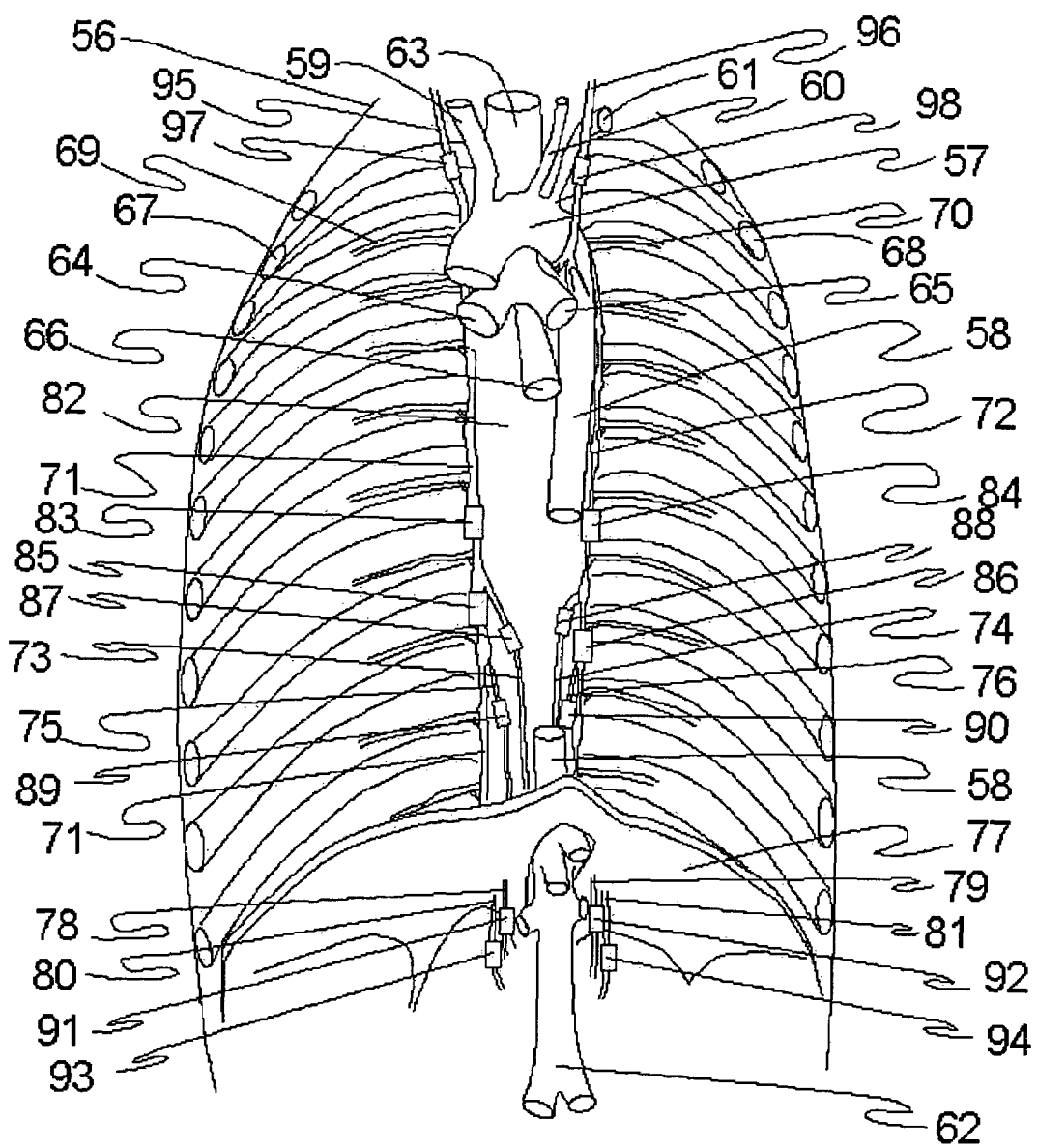
FIG. 14 depicts modulators for GastroPace positioned on the sympathetic trunk and on the greater and lesser splanchnic nerves, both supradiaphragmatically and infradiaphragmatically, for afferent and efferent neural modulation.
Figure 15:
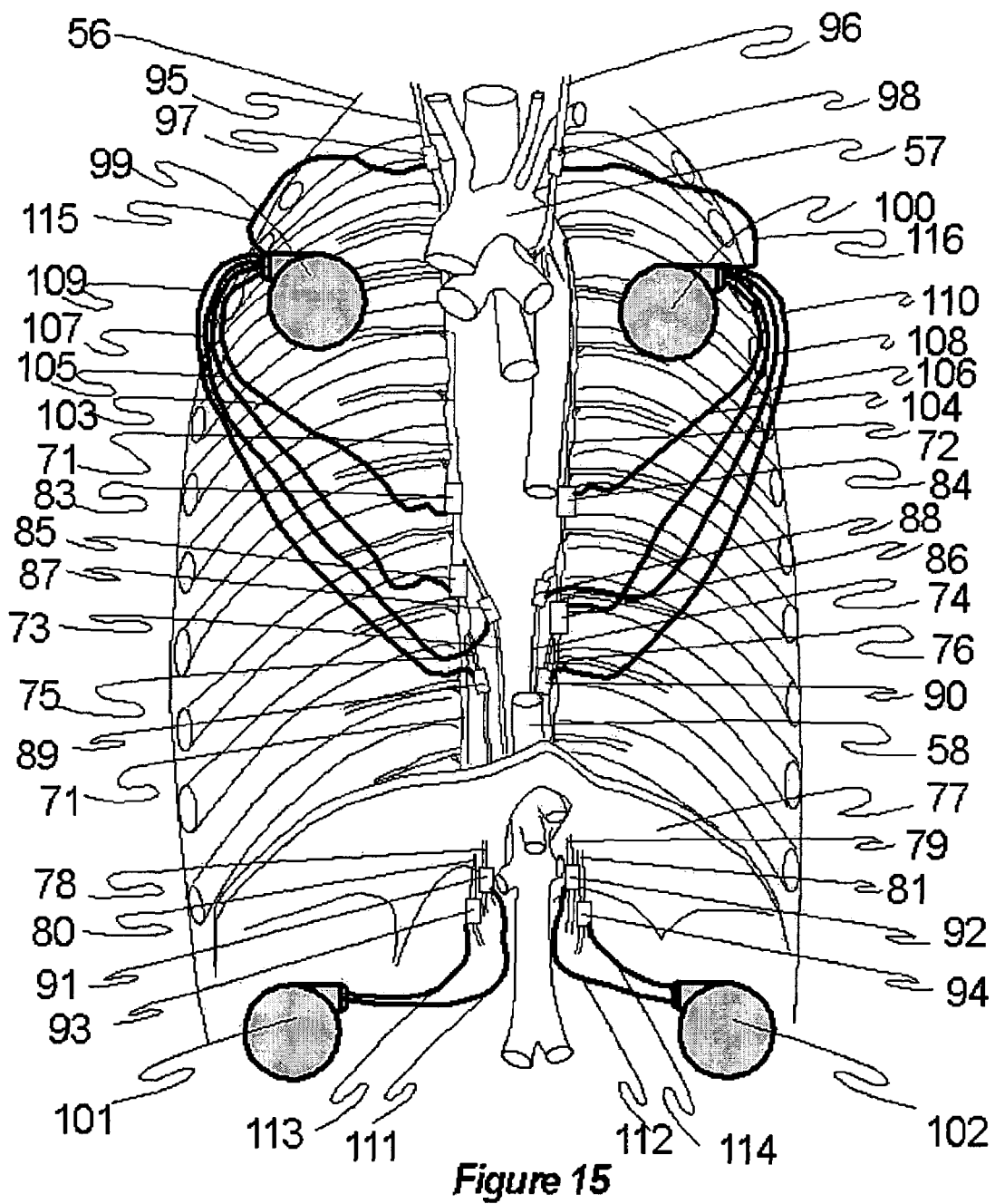
FIG. 15 depicts GastroPace configured with multiple pulse generators, their connecting cables, and multiple modulators positioned on the sympathetic trunk and on the greater and lesser splanchnic nerves, both supradiaphragmatically and infradiaphragmatically, for afferent and efferent neural modulation.
Figure 16:
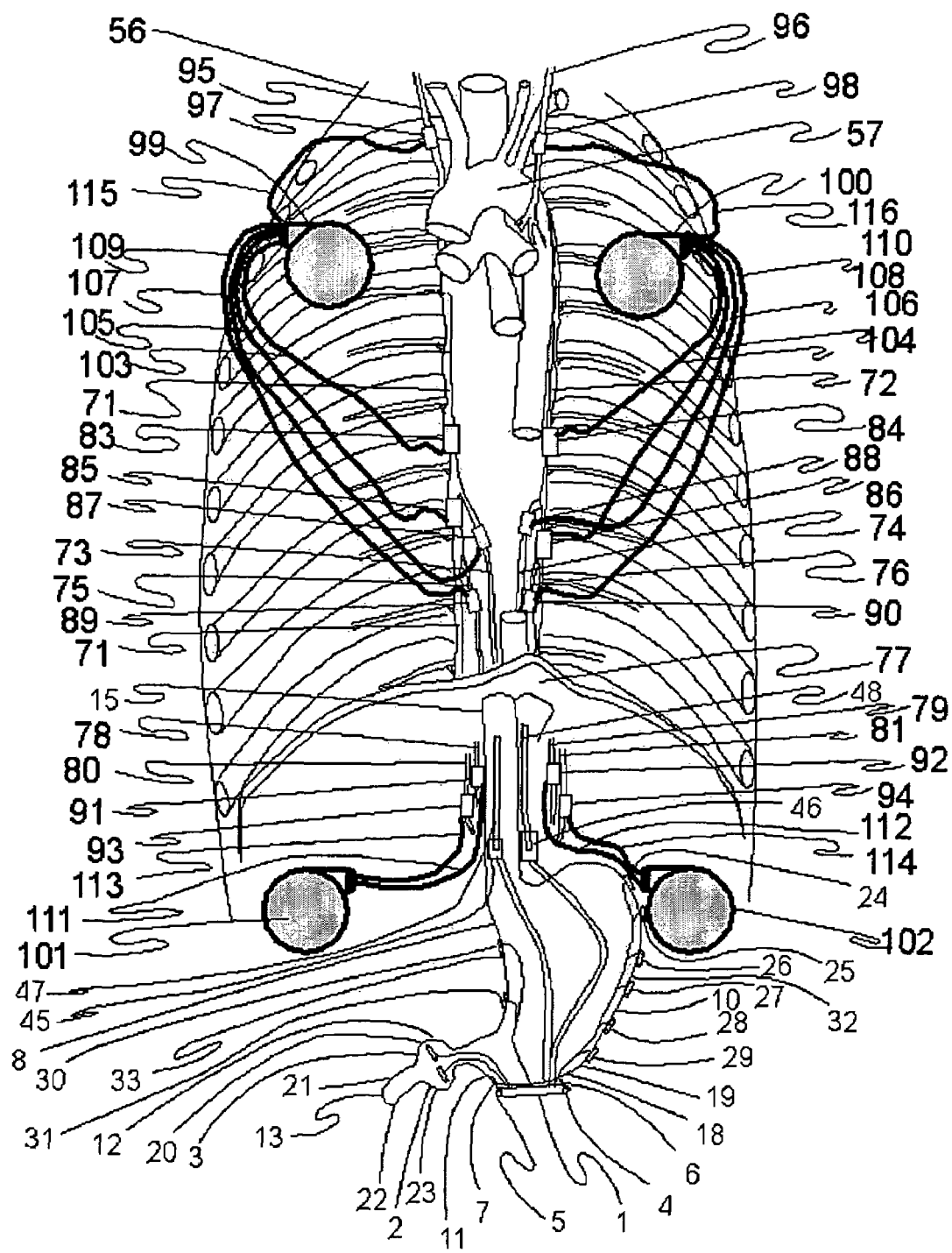
FIG. 16 depicts GastroPace configured with multiple pulse generators, their connecting cables, and multiple modulators positioned on the sympathetic trunk and on the greater and lesser splanchnic nerves, both supradiaphragmatically and infradiaphragmatically, for afferent and efferent neural modulation and with modulators positioned for stimulation of Neural and Neuromuscular structures of the Pylorus, Pyloric Antrum, Greater Curvature, and Lesser Curvature of the Stomach.

The present invention teaches apparatus and method for stimulation of sympathetic afferent fibers using stimulation in the region of the sympathetic trunk. As shown in FIGS. 14, 15, and 16, sympathetic trunk neuromodulatory interface 83 and 85, positioned on right sympathetic trunk 71, and sympathetic trunk neuromodulatory interface 85, 86 positioned on left sympathetic trunk 72, are used to provide stimulation for afferent as well as for efferent sympathetic nervous system modulation. Modulation of efferent sympathetic nervous system is discussed below, and this is used for metabolic modulation.

A1c. Sympathetic Afferents—Other

The present invention teaches apparatus and method for stimulation of sympathetic afferent fibers using stimulation of nerves arising from the sympathetic trunk. As shown in FIGS. 14, 15, and 16, thoracic splanchnic neuromodulatory interface 87, 89, 88, and 90, positioned on right greater splanchnic nerve 73, right lesser splanchnic nerve 75, left greater splanchnic nerve 74, left lesser splanchnic nerve 76, respectively, and are used to provide stimulation for afferent as well as for efferent sympathetic nervous system modulation. Modulation of efferent sympathetic nervous system is discussed below, and this is used for metabolic modulation.

A2. Gastric Musculature Stimulation

A further object of the present invention is the stimulation of the gastric musculature. This may be performed using either or both of closed loop and open loop control. In the present embodiment, a combination of open and closed loop control is employed. The open loop control provides a baseline level of gastric stimulation. This stimulation maintains tone of the gastric musculature. This increases the wall tension the stomach and plays a role in the perception of satiety in the implanted patient. Additionally, stimulation of the gastric musculature causes contraction of the structures, thereby reducing the volume of the stomach. This gastric muscle contraction, and the consequent reduction of stomach volume effectively restricts the amount of food that may be ingested. Surgical techniques have been developed and are known to those practicing in the field of surgical treatment of obesity. Several of these procedures are of the restrictive type, but because of their surgical nature they are fixed in magnitude and difficult if not impossible to reverse. The present invention teaches a technique which employs neural modulation and gastric muscle stimulation which by its nature is the variable and reversible. This offers the advantages postoperative adjustment of magnitude, fine tuning for the individual patient, varying of magnitude to suit the patient's changing needs and changing anatomy over time, and the potential for reversal or termination of treatment. Furthermore, since the gastric wall tension is generated in a physiological manner by the muscle itself, it does not have the substantial risk of gastric wall necrosis and rupture inherent in externally applied pressure, as is the case with gastric banding.

FIGS. 1, 2, and 3 depict placements of the implantable pulse generator 1 that may be used to stimulate gastric muscle tissue. Stimulation of both longitudinal and circular muscle layers is included in the present invention. Stimulation of gastric circular muscle layer causes circumferential contraction of the stomach, and stimulation of gastric longitudinal muscle layer causes longitudinal contraction of the stomach.

This muscle stimulation and contraction accomplishes several objectives: (1) functional reduction in stomach volume, (2) increase in stomach wall tension, (3) reduction in rate of food bolus flow. All of these effects are performed to induce the sensation of satiety.

A3. Gastric Pylorus Stimulation

Figure 4:
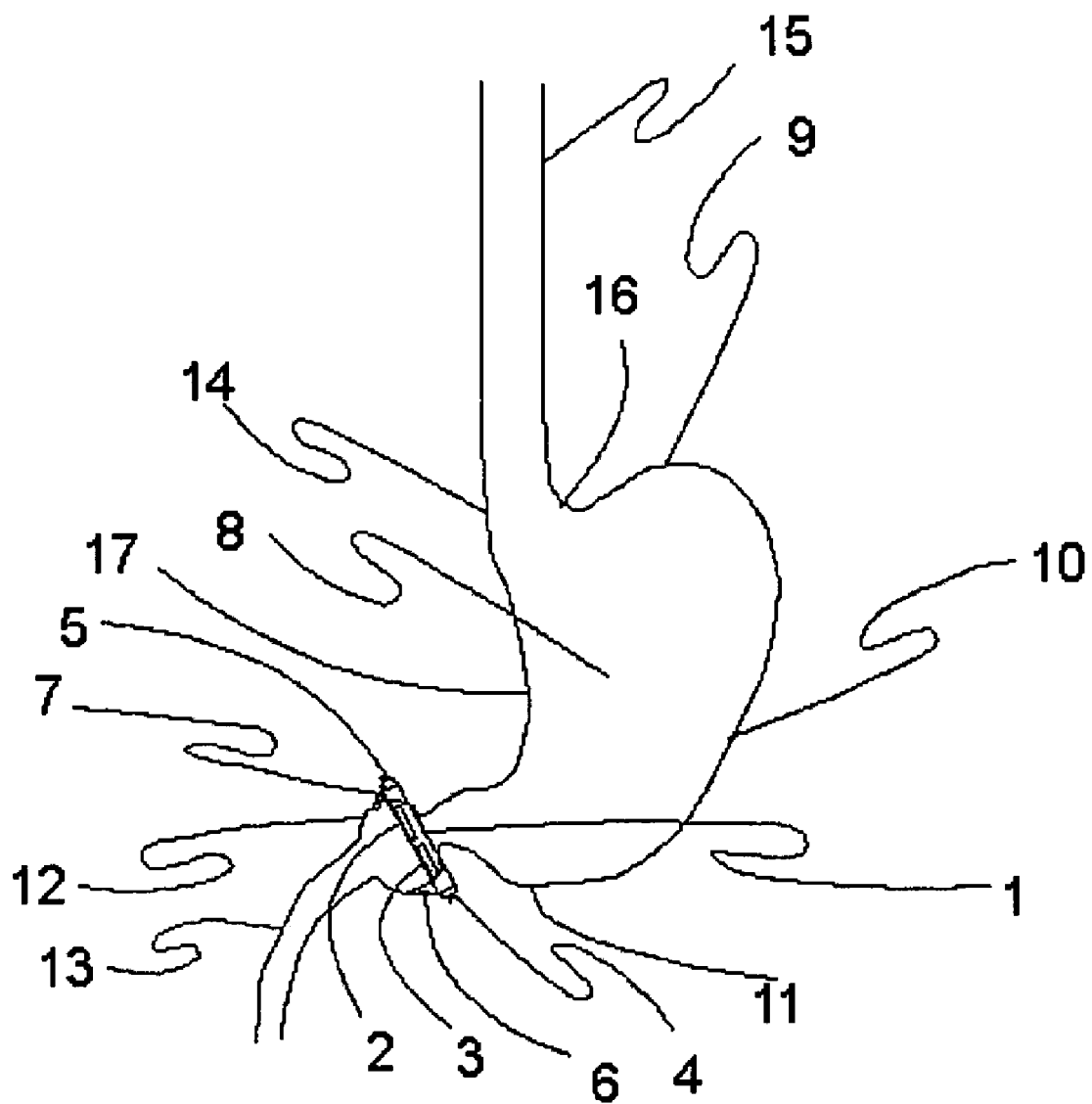
FIG. 4 depicts GastroPace implanted adjacent to the Gastric Pylorus for modulation of pylorus activity and consequent control of gastric food efflux and intraluminal pressure.

FIG. 4 depicts implantable pulse generator 1 positioned to perform stimulation of the gastric pylorus 12 to induce satiety by restricting outflow of food bolus material from the stomach 8 into the duodenum 13. Stimulation of the pylorus 12 may be continuous, intermittent, or triggered manually or by sensed event or physiological condition. FIG. 4 depicts implantable pulse generator 1 positioned adjacent to the gastric pylorus 12; this position provides secure modulator positioning while eliminating the risk of modulator and wire breakage inherent in other designs in which implantable pulse generator 1 is positioned remote from the gastric pylorus 12.

Figure 5:
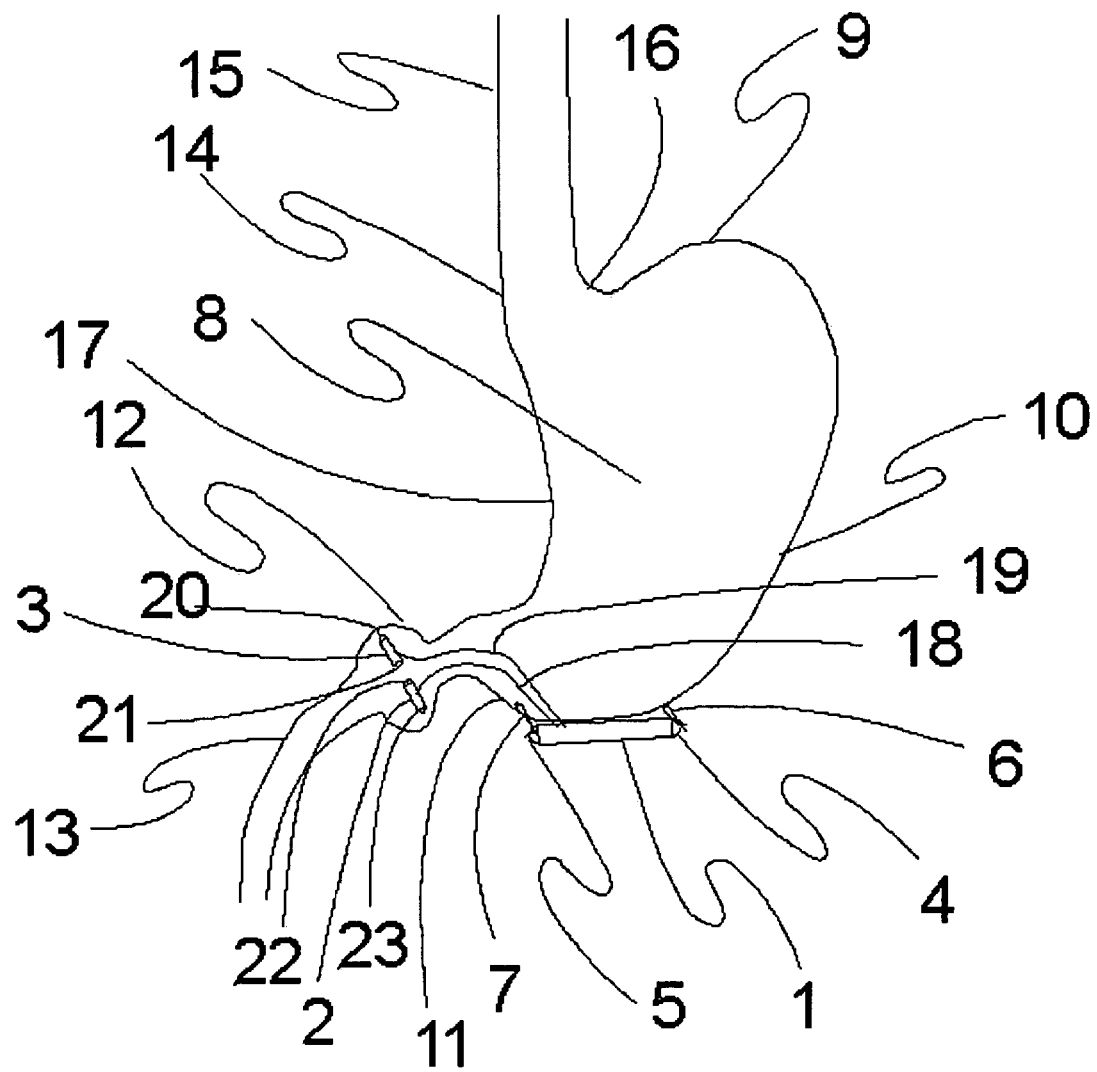
FIG. 5 depicts GastroPace implanted along the Pyloric Antrum of the stomach with modulators positioned for stimulation of Neural and Neuromuscular structures of the Pylorus and Pyloric Antrum of the Stomach.

FIG. 5 depicts implantable pulse generator 1 positioned to perform stimulation of the gastric pylorus 12 to induce satiety by restricting outflow of food bolus material from the stomach 8 into the duodenum 13. Stimulation of the pylorus 12 may be continuous, intermittent, or triggered manually or by sensed event or physiological condition. FIG. 5 depicts implantable pulse generator 1 attached to stomach 8, specifically by the pyloric antrum 11; this position facilitates the use of a larger implantable pulse generator 1. The risk of modulator and wire breakage is minimized by the use of appropriate strain relief and stranded wire designs.

A4. Parasympathetic Simulation

The parasympathetic nervous system is complementary to the sympathetic nervous system and plays a substantial role in controlling digestion and cardiac activity. Several routes are described in the present invention to modulate activity of the parasympathetic nervous system.

A4a. Parasympathetic Stimulation—Vagus Nerve

Others have advocated the use of vagus nerve stimulation for the treatment of a number of disorders including obesity. Zabara and others have described systems in which the vagus nerve in the region of the neck is stimulated. This is plagued with a host of problems, including life-threatening cardiac complications as well as difficulties with speech and discomfort during stimulation. The present invention is a substantial advance over that discussed by Zabara et al, in which unrestricted fiber activation using epineural stimulation is described. That technique results in indiscriminate stimulation of efferent and afferent fibers. With vagus nerve stimulation, efferent fiber activation generates many undesirable side effects, including gastric and duodenal ulcers, cardiac disturbances, and others.

In the present invention, as depicted in FIG. 14, vagus neuromodulatory interface 97 and 98 are implanted adjacent to and in communication with right vagus nerve 95 and left vagus nerve 96. The neuromodulatory interface 97 and 98 overcomes these limitations that have persisted for over a decade with indiscriminate vagus nerve stimulation, by selectively stimulating afferent fibers of the at least one of the vagus nerve, the sympathetic nerves, and other nerves. The present invention includes the selective stimulation of afferent fibers using a technique in which electrical stimulation is used to block anterograde propagation of action potentials along the efferent fibers. The present invention includes the selective stimulation of afferent fibers using a technique in which stimulation is performed proximal to a nerve transection and in which the viability of the afferent fibers is maintained. One such implementation involves use of at least one of neuromodulatory interface 34 which is of the form shown in at least one of Longitudinal Electrode Neuromodulatory Interface 118, Longitudinal Electrode Regeneration Port Neuromodulatory Interface 119, Regeneration Tube Neuromodulatory Interface 120, or other design in which a subset of the neuronal population is modulated.

A.4.a.i. Innovative Stimulation Anatomy

Figure 6:
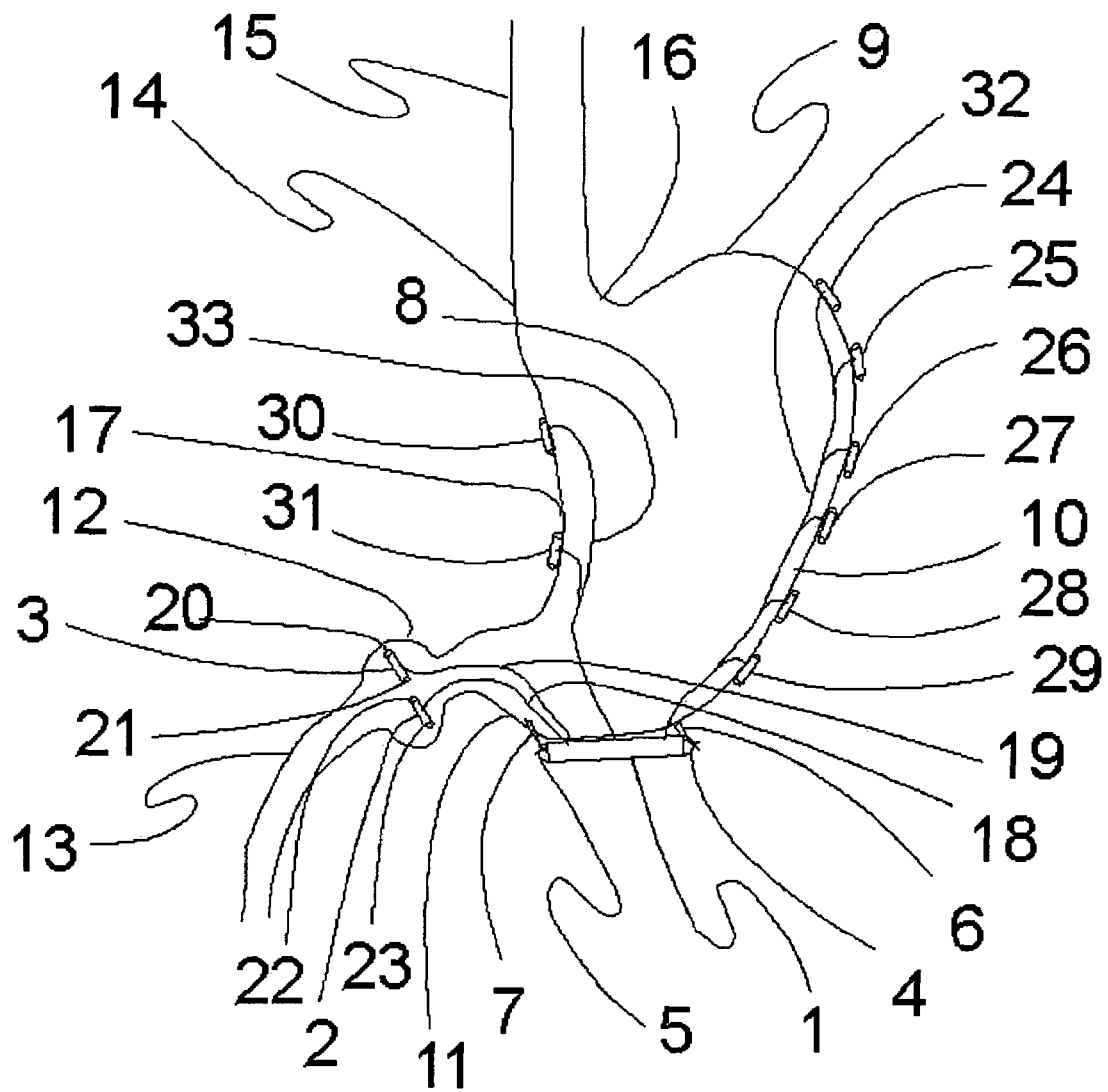
FIG. 6 depicts GastroPace implanted along the Pyloric Antrum of the stomach with modulators positioned for stimulation of Neural and Neuromuscular structures of the Pylorus, Pyloric Antrum, Greater Curvature, and Lesser Curvature of the Stomach.

FIG. 6 depicts multimodal treatment for the generation of satiety, using sympathetic stimulation, gastric muscle stimulation, gastric pylorus stimulation, and vagus nerve stimulation. This is described in more detail below. Modulators 30 and 31 are positioned in the general region of the lesser curvature of stomach 17. Stimulation in this region results in activation of vagus nerve afferent fibers. Stimulation of other regions may be performed without departing from the present invention. In this manner, selective afferent vagus nerve stimulation may be achieved, without the detrimental effects inherent in efferent vagus nerve stimulation, including cardiac rhythm disruption and induction of gastric ulcers.

A.4.a.ii. Innovative Stimulation Device

The present invention further includes devices designed specifically for the stimulation of afferent fibers.

Figure 7:
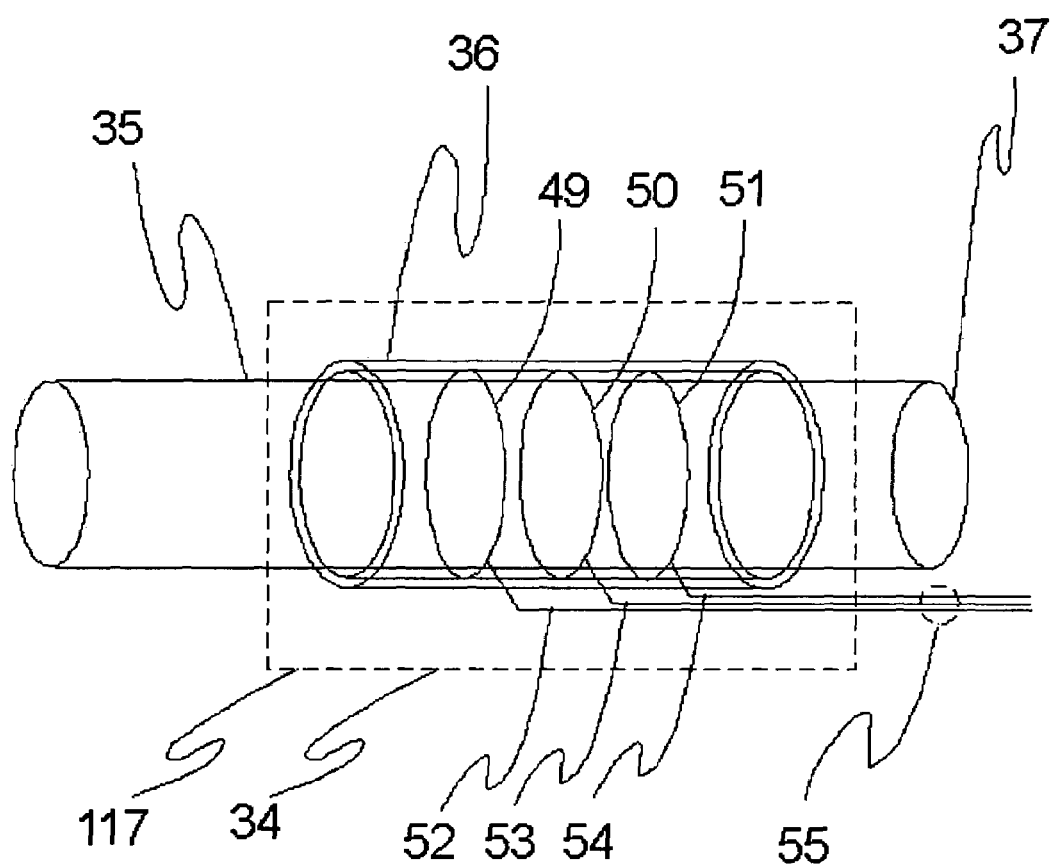
FIG. 7 depicts the Nerve Cuff Electrode, comprising the Epineural Electrode Nerve Cuff Design.

FIG. 7 depicts epineural cuff electrode neuromodulatory interface 117, one of several designs for neuromodulatory interface 34 included in the present invention. Nerve 35 is shown inserted through nerve cuff 36. For selective afferent stimulation, the nerve 35 is transected distal to the epineural cuff electrode neuromodulatory interface 117. This case is depicted here, in which transected nerve end 37 is seen distal to epineural cuff electrode neuromodulatory interface 117. Epineural electrode-49, 50, and 51 are mounted along the inner surface of nerve cuff 36 and in contact or close proximity to nerve 35. Epineural electrode connecting wire 52, 53, 54 are electrically connected on one end to epineural electrode 49, 50, and 51, respectively, and merge together on the other end to form connecting cable 55.

Figure 8:
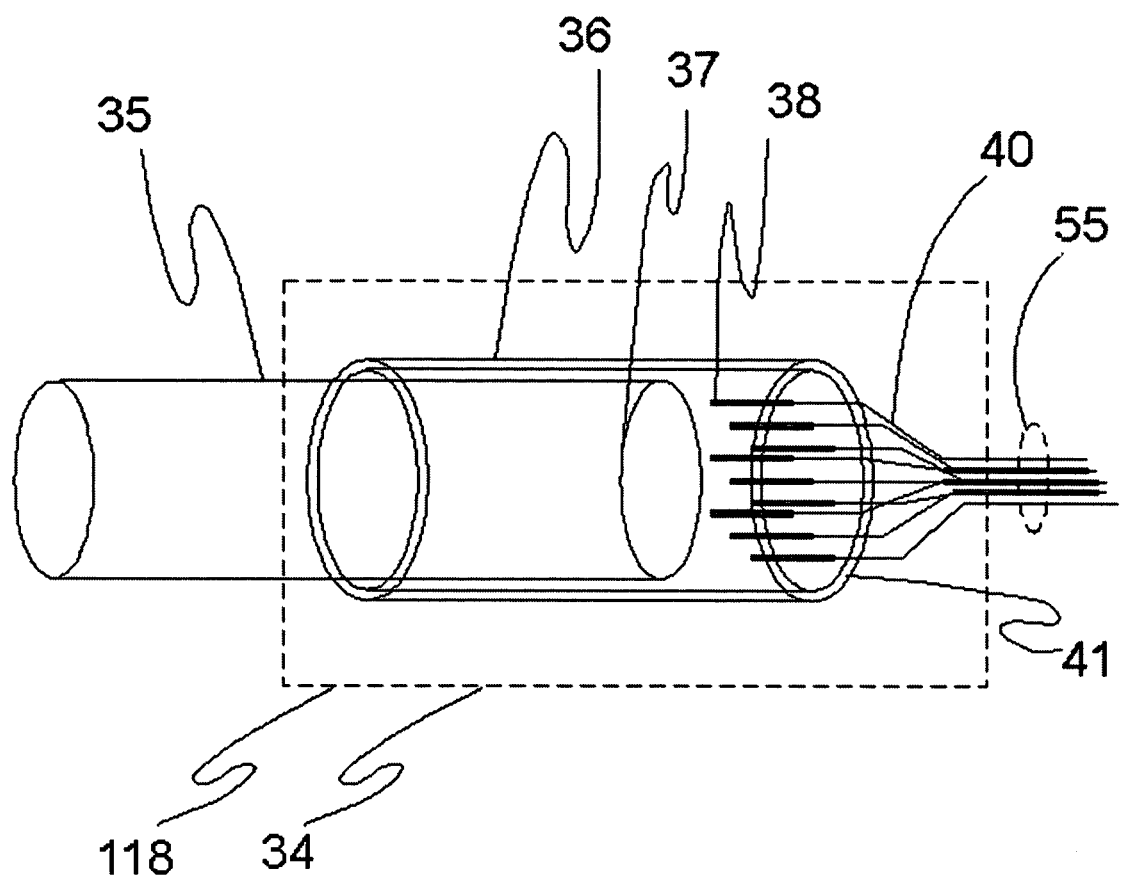
FIG. 8 depicts the Nerve Cuff Electrode, comprising the Axial Electrode Blind End Port Design.

FIG. 8 depicts longitudinal electrode neuromodulatory interface 118, one of several designs for neuromodulatory interface 34 included in the present invention. Nerve 35 is shown inserted into nerve cuff 36. For selective afferent stimulation, the nerve 35 is transected prior to surgical insertion into nerve cuff 36. Longitudinal electrode array 38 is mounted within nerve cuff 36 and in contact or close proximity to nerve 35. Connecting wire array 40 provides electrical connection from each element of longitudinal electrode array 38 to connecting cable 55. Nerve cuff end plate 41 is attached to the distal end of nerve cuff 36. Nerve 35 may be advanced sufficiently far into longitudinal electrode array 38 such that elements of longitudinal electrode array-38 penetrate into nerve 35. Alternatively, nerve 35 may be placed with a gap between transected nerve end 37 and longitudinal electrode array 38 such that neural regeneration occurs from transected nerve end 37 toward and in close proximity to elements of longitudinal electrode array 38.

Figure 9:
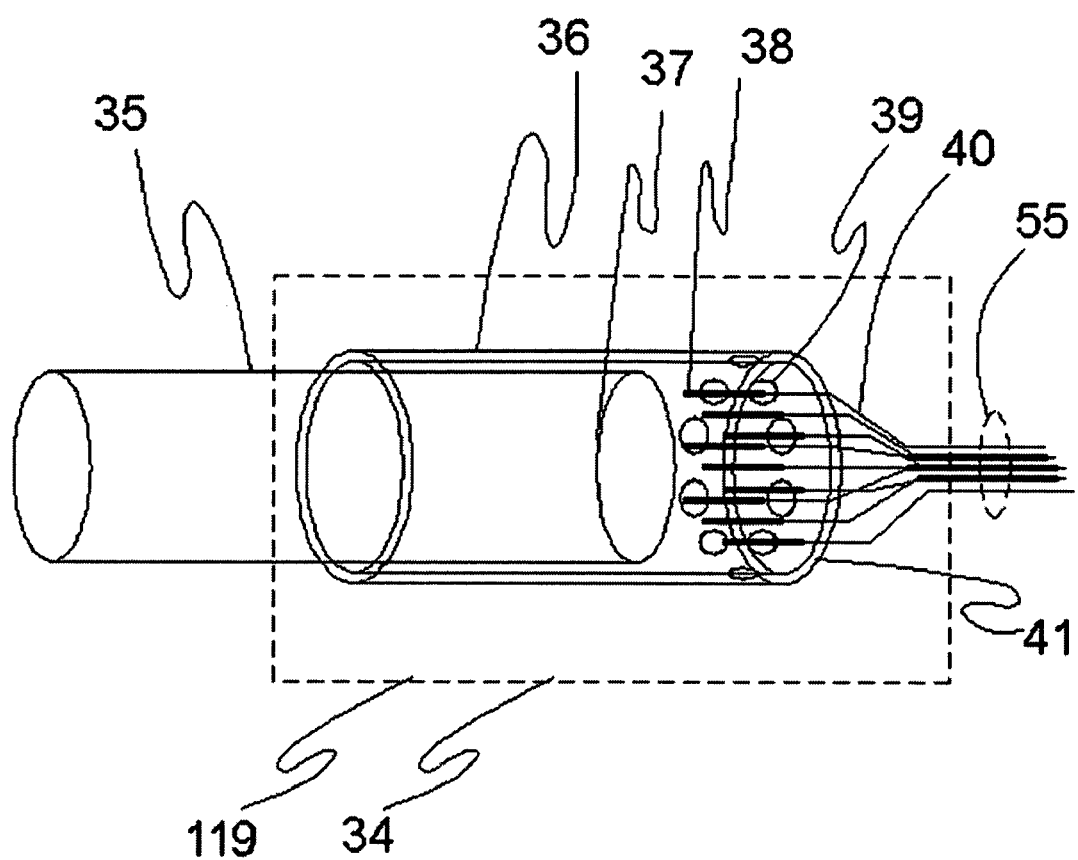
FIG. 9 depicts the Nerve Cuff Electrode, comprising the Axial Electrode Regeneration Port Design.

FIG. 9 depicts longitudinal electrode regeneration port neuromodulatory interface 119, an improved design for neuromodulatory interface 34 included in the present invention. Nerve 35 is shown inserted into nerve cuff 36. For selective afferent stimulation, the nerve 35 is transected prior to surgical insertion into nerve cuff 36. Longitudinal electrode array 38 is mounted within never cuff 36 and in contact or close proximity to nerve 35. Connecting wire array 40 provides electrical connection from each element of longitudinal electrode array 38 to connecting cable 55. Nerve cuff end plate 41 is attached to the distal end of nerve cuff 36. Nerve 35 may be advanced sufficiently far into longitudinal electrode array 38 such that elements of longitudinal electrode array 38 penetrate into nerve 35. Alternatively, nerve 35 may be placed with a gap between transected nerve end 37 and longitudinal electrode array 38 such that neural regeneration occurs from transected nerve end 37 toward and in close proximity to elements of longitudinal electrode array 38. At least one of nerve cuff 36 and nerve cuff end plate 41 are perforated with one or a multiplicity of regeneration port 39 to facilitate and enhance regeneration of nerve fibers from transected nerve end 37.

Figure 10:
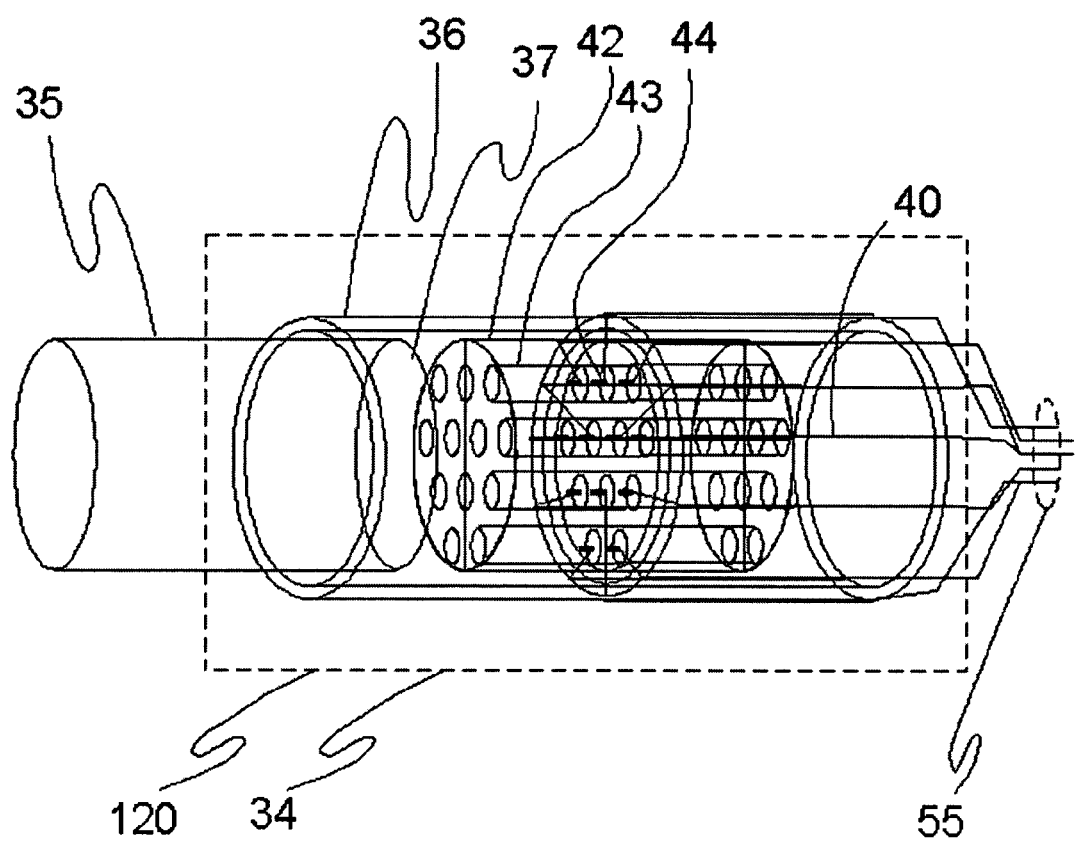
FIG. 10 depicts the Nerve Cuff Electrode, comprising the Axial Regeneration Tube Design.

FIG. 10 depicts regeneration tube neuromodulatory interface 120, an advanced design for neuromodulatory interface 34 included in the present invention. Nerve 35 is shown inserted into nerve cuff 36. For selective afferent stimulation, the nerve 35 is transected prior to surgical insertion into nerve cuff 36. Regeneration electrode array 44 is mounted within regeneration tube array 42, which is contained within nerve cuff 36. Each regeneration tube 43 contains at least one element of regeneration electrode array 44. Each element of regeneration electrode array 44 is electrically connected by at least one element of connecting wire array 40 to connecting cable 55. Nerve 35 may be surgically inserted into nerve cuff 36 sufficiently far to be adjacent to regeneration tube array 42 or may be placed with a gap between transected nerve end 37 and regeneration tube array 42. Neural regeneration occurs from transected nerve end 37 toward and through regeneration tube 43 elements regeneration tube array 42.

The present invention further includes stimulation of other tissues that influence vagus nerve activity. These include tissues of the esophagus, stomach, small and large intestine, pancreas, liver, gallbladder, kidney, mesentery, appendix, bladder, uterus, and other intraabdomnial tissues. Stimulation of one or a multiplicity of these tissues modulates activity of the vagus nerve afferent fibers without significantly altering activity of efferent fibers. This method and the associated apparatus facilitates the stimulation of vagus nerve afferent fibers without activating vagus nerve efferent fibers, thereby overcoming the ulcerogenic and cardiac side effects of nonselective vagus nerve stimulation. This represents a major advance in vagus nerve modulation and overcomes the potentially life-threatening complications of nonselective stimulation of the vagus nerve.

A4b. Parasympathetic Stimulation—Other

The present invention teaches stimulation of the cervical nerves or their roots or branches for modulation of the parasympathetic nervous system. Additionally, the present invention teaches stimulation of the sacral nerves of their roots or branches for modulation of the parasympathetic nervous system.

A5. Multichannel Satiety Modulation

FIG. 6 depicts apparatus and method for performing multichannel modulation of satiety. Implantable pulse generator 1 is attached to stomach 8, via attachment means 6 and 7 connected from stomach 8 to attachment fixture 4 and 5, respectively. Implantable pulse generator 1 is electrically connected via modulator cable 32 to modulators 24, 25, 26, 27, 28, and 29, which are affixed to the stomach 8 preferably along the region of the greater curvature of stomach 10. Implantable pulse generator 1 is additionally electrically connected via modulator cable 33 to modulators 30 and 31, which are affixed to the stomach 8 preferably along the region of the lesser curvature of stomach 17. Implantable pulse generator 1 is furthermore electrically connected via modulator cable 18 and 19 to modulators 2 and -3, respectively, which are affixed to the gastric pylorus 12. Modulator 2 is affixed to gastric pylorus via modulator attachment fixture 22 and 23, and modulator 3 is affixed to gastric pylorus via modulator attachment fixture 20 and 21.

Using the apparatus depicted in FIG. 6, satiety modulation is achieved through multiple modalities. A multiplicity of modulators, including modulator 30 and 31 facilitate stimulation of vagus and sympathetic afferent fibers directly, as well as through stimulation of tissues, including gastric muscle, that in turn influence activity of the sympathetic and vagus afferent fibers. A multiplicity of modulators, including modulator 24, 25, 26, 27, 28, and 29 facilitate stimulation of sympathetic afferent fibers directly, as well as through stimulation of tissues, including gastric muscle, that in turn influence activity of the sympathetic fibers. Any of these modulators may be used to modulate vagus nerve activity; however, one advancement taught in the present invention is the selective stimulation of sympathetic nerve fiber activation, and this is facilitated by modulators 24, 25, 26, 27, 28, and 29, by virtue of their design for and anatomical placement in regions of the stomach 8 that are not innervated by the vagus nerve or its branches.

In addition to the apparatus and methods depicted in FIG. 6 for satiety modulation, the present invention further includes satiety modulation performed with the apparatus depicted in FIG. 16, and described previously, using stimulation of right sympathetic trunk 71, left sympathetic trunk 72, right greater splanchnic nerve 73, left greater splanchnic nerve 74, right lesser splanchnic nerve 75, left lesser splanchnic nerve 76 or other branch or the sympathetic nervous system.

B. Metabolic Modulation

B.1. Sympathetic Efferent Stimulation

One objective of the modulator configuration employed in the present invention is the selected stimulation of sympathetic efferent nerve fibers. The present invention includes a multiplicity of potential modulator configurations and combinations of thereof. The present embodiment includes modulators placed at a combination of sites to interface with the sympathetic efferent fibers. These sites include the musculature of the stomach, the distal sympathetic branches penetrating into the stomach, postganglionic axons and cell bodies, preganglionic axons and cell bodies, the sympathetic chain and portions thereof, the intermediolateral nucleus, the locus ceruleus, the hypothalamus, and other structures comprising or influencing activity of the sympathetic nervous system.

Stimulation of the sympathetic efferents is performed to elevate the metabolic rate and lipolysis in the adipose tissue, thereby enhancing breakdown of fat and weight loss in the patient.

B.1a. Sympathetic Efferent Stimulation Sympathetic Trunk

FIGS. 14, 15, and 16 depict apparatus for stimulation of the sympathetic nervous system. FIG. 14 depicts a subset of anatomical locations for placement of neuromodulatory interfaces for modulation of the sympathetic nervous system. FIG. 15 depicts the same apparatus with the further addition of a set of implantable pulse generator 1 and connecting cables. FIG. 16 depicts the apparatus shown in FIG. 15 with the further addition of gastric modulation apparatus also depicted in FIG. 6.

Figure 13:
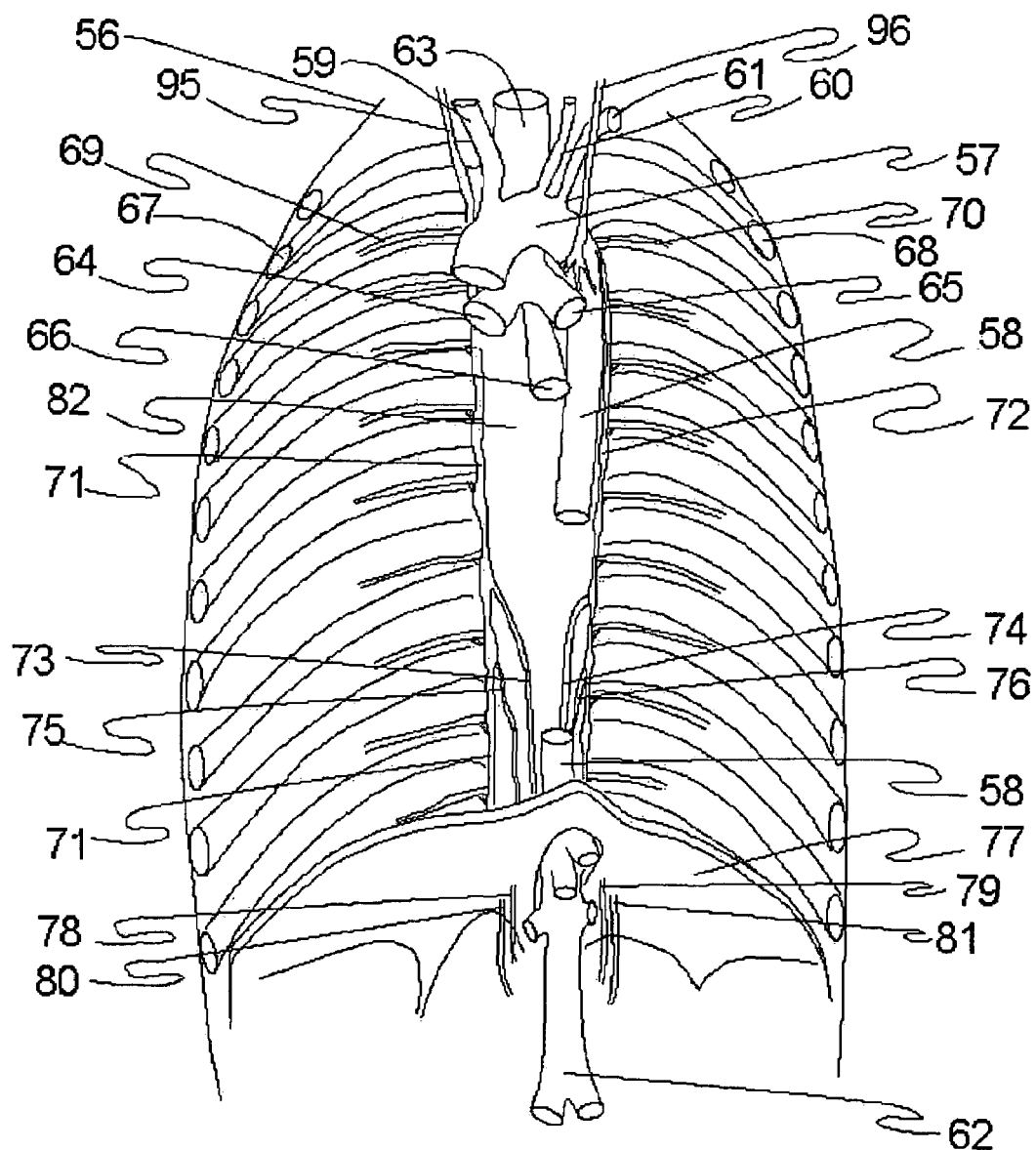
FIG. 13 depicts the Normal Thoracoabdominal anatomy as seen via a saggital view of an open dissection.

FIG. 13 reveals the normal anatomy of the thoracic region. Trachea 63 is seen posterior to aortic arch 57. Brachiocephalic artery 59, left common carotid artery-60 arise from aortic arch 57, and left subclavian artery 61 arises from the left common carotid artery 60. Right mainstream bronchus 64 and left mainstream bronchus 65 arise from trachea 63. Thoracic descending aorta 58 extends from aortic arch 57 and is continuous with abdominal aorta 62. Right vagus nerve 95 and left vagus nerve 96 are shown. Intercostal nerve 69 and 70 are shown between respective pairs of ribs, of which rib 67 and rib 68 are labeled.

Right sympathetic trunk 71 and left sympathetic trunk are lateral to mediastinum 82. Right greater splanchnic nerve 73 and right lesser splanchnic nerve 75 arise from right sympathetic trunk 71. Left greater splanchnic nerve 74 and left lesser splanchnic nerve 76 arise from left sympathetic trunk 72. Right subdiaphragmatic greater splanchnic nerve 78, left subdiaphragmatic greater splanchnic nerve 79, right subdiaphragmatic lesser splanchnic nerve 80, and left subdiaphragmatic lesser splanchnic nerve 81 are extensions below the diaphragm 77 of the right greater splanchnic nerve 73, left greater splanchnic nerve 74, right lesser splanchnic nerve 75, and left lesser splanchnic nerve 76, respectively.

B.1.b. Sympathetic Efferent Stimulation—Splanchnics

FIG. 14 depicts multichannel sympathetic modulation implanted with relevant anatomical structures. Sympathetic trunk neuromodulatory interface 83 and 85 are implanted adjacent to and in communication with right sympathetic trunk 71. Sympathetic trunk neuromodulatory interface 84 and 86 are implanted adjacent to and in communication with left sympathetic trunk 72. Sympathetic trunk neuromodulatory interface 83, 84, 85, and 86 are implanted superior to their respective sympathetic trunk levels at which the right greater splanchnic nerve 73, left greater splanchnic nerve 74, right lesser splanchnic nerve 75, and left lesser splanchnic nerve 76, arise, respectively.

Thoracic splanchnic nerve interface 87, 88, 89, 90 are implanted adjacent to and in communication with the right greater splanchnic nerve 73, left greater splanchnic nerve 74, right lesser splanchnic nerve 75, and left lesser splanchnic nerve 76, arise, respectively. Abdominal splanchnic nerve interface 91, 92, 93, and 94 are implanted adjacent to an in communication with the right subdiaphragmatic greater splanchnic nerve 78, left subdiaphragmatic greater splanchnic nerve 79, right subdiaphragmatic lesser splanchnic nerve 80, and left subdiaphragmatic lesser splanchnic nerve 81, respectively.

Stimulation of at least one of right sympathetic trunk 71, left sympathetic trunk 72, right greater splanchnic nerve 73, left greater splanchnic nerve 74, right lesser splanchnic nerve 75, and left lesser splanchnic nerve 76, right subdiaphragmatic greater splanchnic nerve 78, left subdiaphragmatic greater splanchnic nerve 79, right subdiaphragmatic lesser splanchnic nerve 80, and left subdiaphragmatic lesser splanchnic nerve 81 enhances metabolism of adipose tissue. Stimulation of these structures may be performed using at least one of electrical energy, electrical fields, optical energy, mechanical energy, magnetic energy, chemical compounds, pharmacological compounds, thermal energy, vibratory energy, or other means for modulating neural activity.

FIG. 15 depicts the implanted neuromodulatory interfaces as in FIG. 14, with the addition of the implanted pulse generators. Implantable pulse generator 99 is connected via connecting cable 103, 105, 107, 109, 115, to sympathetic trunk neuromodulatory interface 83 and 85, and thoracic splanchnic neuromodulatory interface 87 and 89, and vagus neuromodulatory interface 97, respectively. Implantable pulse generator 100 is connected via connecting cable 104, 106, 108, 110, 116, to sympathetic trunk neuromodulatory interface 83 and 85, and thoracic splanchnic neuromodulatory interface 88 and 90, and vagus neuromodulatory interface 98, respectively. Implantable pulse generator 101 is connected via connecting cable 111 and 113 to abdominal splanchnic neuromodulatory interface 91 and 93, respectively. Implantable pulse generator 102 is connected via connecting cable 112 and 114 to abdominal splanchnic neuromodulatory interface 92 and 94, respectively.

B.1.c. Sympathetic Efferent Stimulation—Spinal Cord

Figure 17:
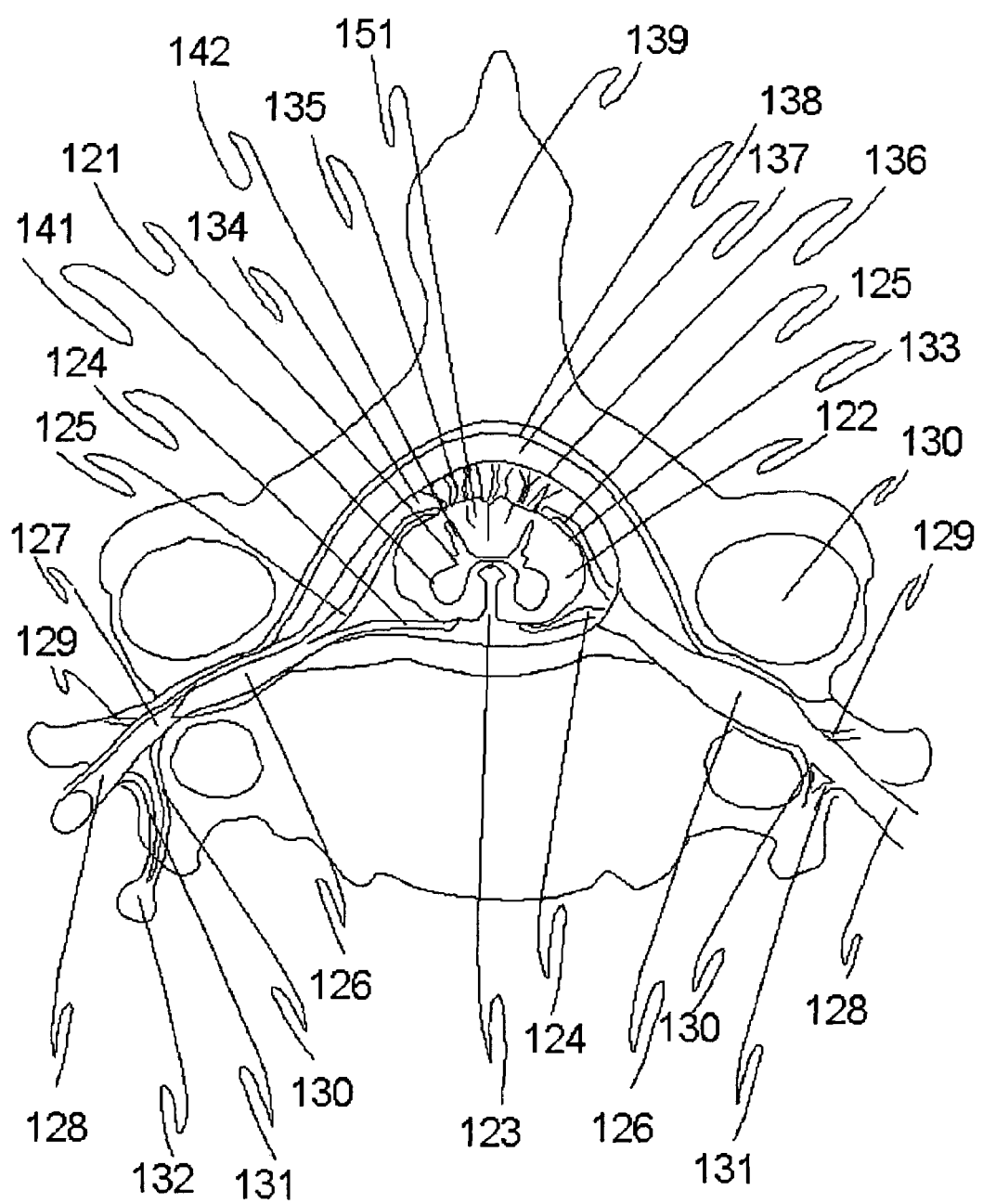
FIG. 17 depicts the Normal Spinal Cord Anatomy, shown in Transverse Section.
Figure 18:
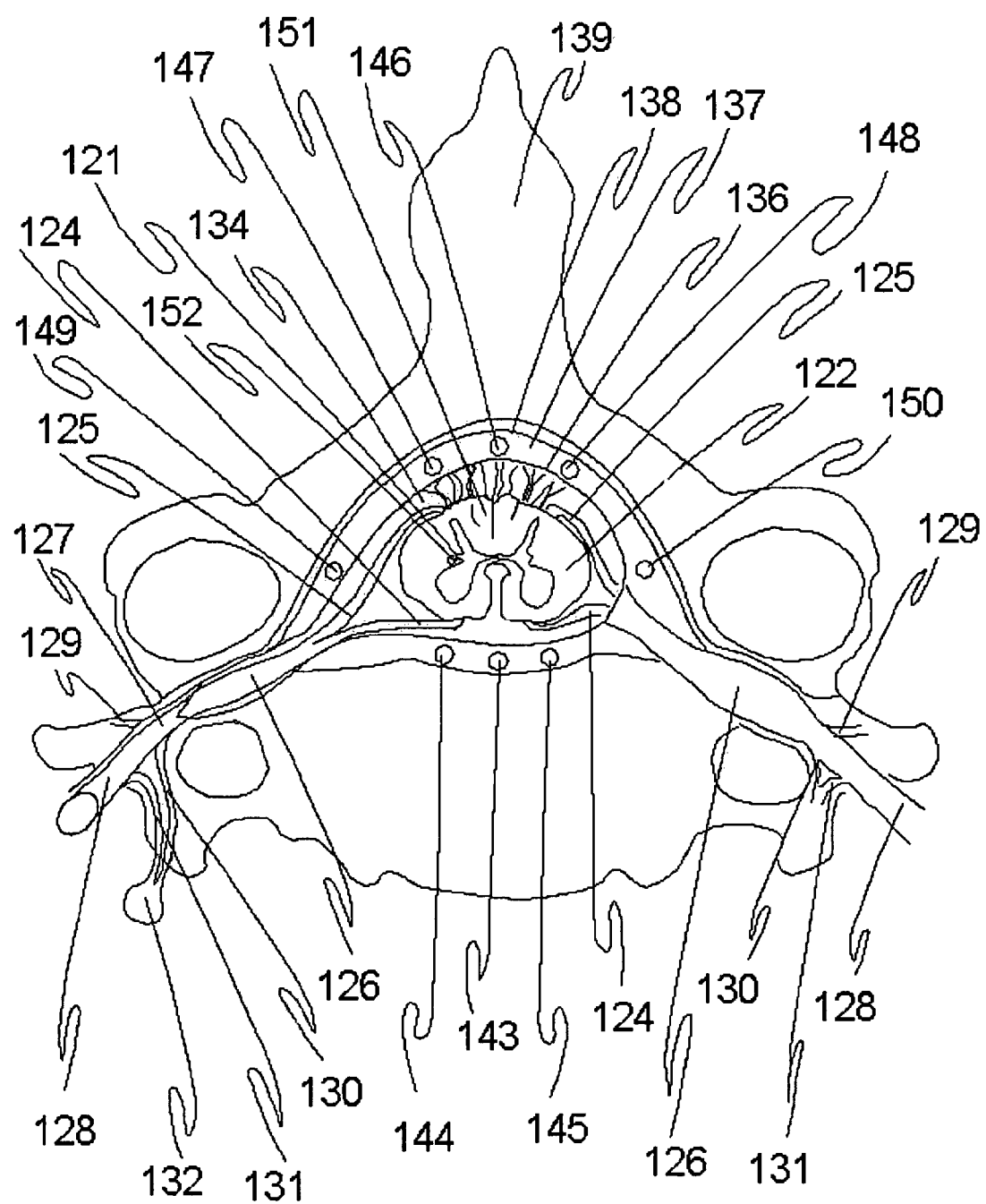
FIG. 18 depicts GastroPace implanted with multiple modulators positioned for modulation of Spinal Cord structures

FIGS. 17 and 18 depicts the normal cross sectional anatomy of the spinal cord 151 and anatomy with implanted neuromodulatory interfaces, respectively.

FIG. 17 depicts the normal anatomical structures of the spinal cord 151, including several of its component structures such as the intermediolateral nucleus 121, ventral horn of spinal gray matter 141, dorsal horn of spinal gray matter 142, spinal cord white matter 122, anterior median fissure 123. Other structures adjacent to or surrounding spinal cord 151 include ventral spinal root 124, dorsal spinal root 125, spinal ganglion 126, spinal nerve 127, spinal nerve anterior ramus 128, spinal nerve posterior ramus 129, gray ramus communicantes 130, white ramus communicantes-131, sympathetic trunk 132, pia mater 133, subarachnoid space 134, arachnoid 135, meningeal layer of dura mater 136, epidural space 137, periosteal layer of dura mater-138, and vertebral spinous process 139, and vertebral facet 140.

FIG. 17 depicts the normal anatomy of the spinal cord seen in transverse section. Spinal cord and related neural structures structures include intermediolateral nucleus 121, spinal cord white matter 122, anterior median fissure 123, ventral spinal root 124, dorsal spinal root 125, spinal ganglion 126, spinal nerve 127, spinal nerve anterior ramus 128, spinal nerve posterior ramus 129, grey ramus communicantes 130, white ramus communicantes 131, sympathetic trunk 132, pia mater 133, subarachnoid space 134, arachnoid 135, meningeal layer of dura 136, epidural space 137, periostial layer of dura mater 138, vertebral spinous process 139, vertebral facet 140, ventral horn of spinal gray matter 141, and dorsal horn of spinal gray matter 142.

FIG. 18 depicts the spinal neuromodulatory interfaces positioned in the vicinity of spinal cord 151. Neuromodulatory interfaces positioned anterior to spinal cord 151 include anterior central spinal neuromodulatory interface 143, anterior right lateral spinal neuromodulatory interface 144, and anterior left lateral spinal neuromodulatory interface 145. Neuromodulatory interfaces positioned posterior to spinal cord 151 include posterior central spinal neuromodulatory interface 146, posterior right lateral spinal neuromodulatory interface 147, and posterior left lateral spinal neuromodulatory interface 148. Neuromodulatory interfaces positioned lateral to spinal cord 151 include right lateral spinal neuromodulatory interface 149 and left lateral spinal neuromodulatory interface 150. Neuromodulatory interfaces positioned within the spinal cord 151 include intermediolateral nucleus neuromodulatory interface-152.

Stimulation, inhibition, or other modulation of the spinal cord 151 is used to modulate fibers of the sympathetic nervous system, including those in the intermediolateral nucleus 121 and efferent and efferent fibers connected to the intermediolateral nucleus 121. Modulation of at least one of portions of the spinal cord-151, intermediolateral nucleus 121, ventral spinal root 124, dorsal spinal root 125, spinal ganglion 126, spinal nerve 127, gray ramus communicantes 130, white ramus communicantes 131 and other structures facilitates modulation of activity of the sympathetic trunk 132. Modulation of activity of the sympathetic truck 132, in turn, is used to modulate at least one of metabolic activity, satiety, and appetite. This may be achieved using intermediolateral nucleus neuromodulatory interface 152, placed in or adjacent to the intermediolateral nucleus 121. The less invasive design employing neuromodulatory interfaces (144, 145, 146, 147, 148, 149, 150) shown positioned in the in epidural space 137 is taught in the present invention.

B.1d. Sympathetic Efferent Stimulation—Other

The present invention further includes modulation of all sympathetic efferent nerves, nerve fibers, and neural structures. These sympathetic efferent neural structures include but are not limited to distal sympathetic nerve branches, mesenteric nerves, sympathetic efferent fibers at all spinal levels, rami communicantes at all spinal levels, paravertebral nuclei, prevertebral nuclei, and other sympathetic structures.

B.2. Noninvasive Stimulation

The present invention teaches a device for metabolic control using tactile stimulation. Tactile stimulation of afferent neurons causes alterations in activity of sympathetic neurons which influence metabolic activity of adipose tissue. The present invention teaches tactile stimulation of skin, dermal and epidermal sensory structures, subcutaneous tissues and structures, and deeper tissues to modulate activity of afferent neurons.

This device for metabolic control employs vibratory actuators. Alternatively, electrical stimulation, mechanical stimulation, optical stimulation, acoustic stimulation, pressure stimulation, and other forms of energy that modulate afferent neural activity, are used.

C. Multimodal Metabolic Modulation

To maximize efficacy while tailoring treatment to minimize side effects, the preferred embodiment includes a multiplicity of treatment modalities, including afferent, efferent, and neuromuscular modulation.

Afferent signals are generated to simulate satiety. This is accomplished through neural, neuromuscular, and hydrostatic mechanisms. Electrical stimulation of the vagus via vagus nerve interface 45 afferents provides one such channel to transmit information to the central nervous system for the purpose of eliciting satiety. Electrical stimulation of the sympathetic afferents via sympathetic nerve interface 46 provides another such channel to transmit information to the central nervous system for the purpose of eliciting satiety. Electrical stimulation of gastric circular muscle layer In FIG. 11, multimodal stimulation is depicted, including stimulation of gastric musculature using modulators 2 and 3, as well as stimulation of afferent fibers of the proximal stump of vagus nerve 47 using vagus nerve modulator 45 and stimulation of afferent fibers of sympathetic nerve branch 48.

Figure 11:
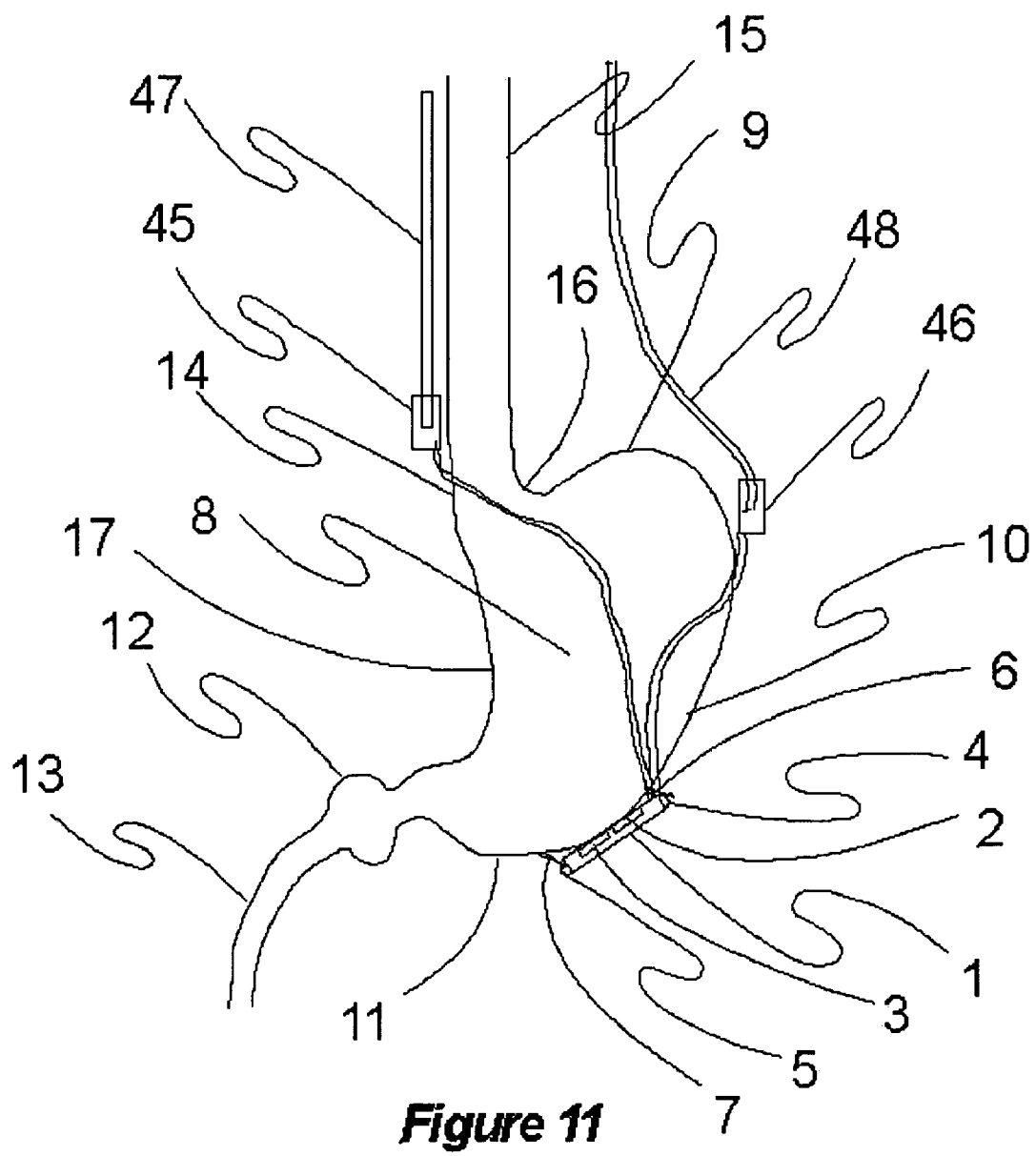
FIG. 11 depicts GastroPace implanted along the Pyloric Antrum of the stomach with modulators positioned for stimulation of Afferent Neural Structures, including sympathetic and parasympathetic fibers.
Figure 12:
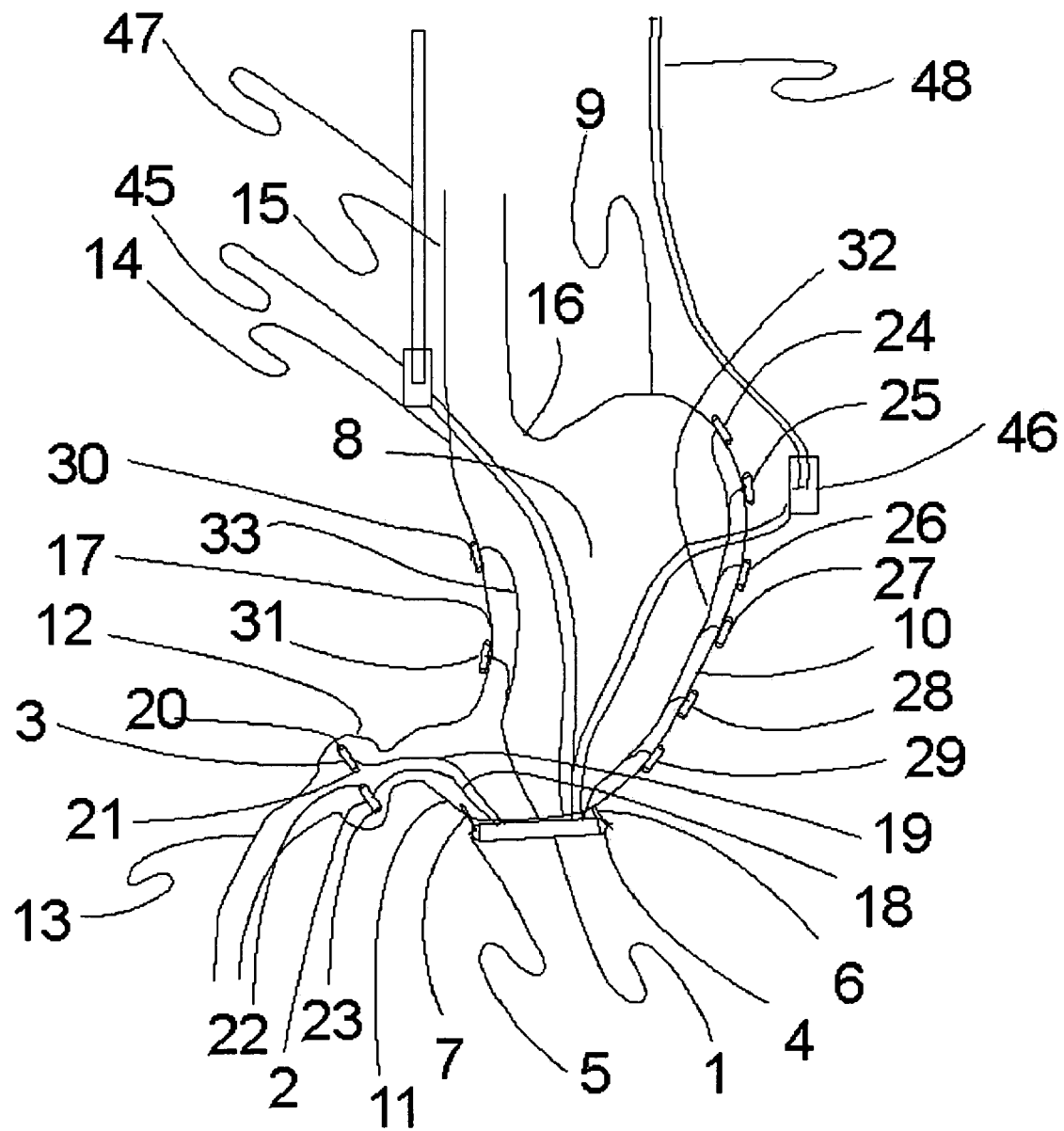
FIG. 12 depicts GastroPace implanted along the Pyloric Antrum of the stomach with modulators positioned for stimulation of Neural and Neuromuscular structures of the Pylorus, Pyloric Antrum, Greater Curvature, and Lesser Curvature of the Stomach and with modulators positioned for stimulation of Afferent Neural Structures, including sympathetic and parasympathetic fibers.

In FIG. 12, expanded multimodal stimulation is depicted, including those modalities shown in FIG. 11, including stimulation of gastric musculature using modulators 2 and 3, as well as stimulation of afferent fibers of the proximal stump of vagus nerve 47 using vagus nerve modulator 45 and stimulation of afferent fibers of sympathetic nerve branch 48. In addition to those modalities shown in FIG. 6, explained in detail above, including modulation of gastric muscular fibers, sympathetic afferent fibers innervating gastric tissues, and vagus afferent fibers innervating gastric tissues.

In FIG. 16, further expanded multimodal modulation is depicted, including modalities encompassed and described above and depicted in FIG. 15 and FIG. 12. This includes modulation of gastric muscle fibers, fibers of the sympathetic nerve branch 48 and vagus nerve 47 that innervate gastric tissues, and a multiplicity of structures in the sympathetic nervous system and vagus nerve 47.

E. System/Pulse Generator Design

Neuromodulatory interfaces that use electrical energy to modulate neural activity may deliver a broad spectrum of electrical waveforms. One preferred set of neural stimulation parameter sets includes pulse frequencies ranging from 0.1 Hertz to 1000 Hertz, pulse widths from 1 microsecond to 500 milliseconds. Pulses are charge balanced to insure no net direct current charge delivery. The preferred waveform is bipolar pulse pair, with an interpulse interval of 1 microsecond to 1000 milliseconds. Current regulated stimulation is preferred and includes pulse current amplitudes ranging from 1 microamp to 1000 milliamps. Alteratively, voltage regulation may be used, and pulse voltage amplitudes ranging from 1 microamp to 1000 milliamps. These parameters are provided as exemplary of some of the ranges included in the present invention; variations from these parameter sets are included in the present invention.

| FIG. | Description |
| --- | --- |
| 1 | GastroPace - Superior Greater Curvature Neuromuscular Stimulation Configuration |
| 2 | GastroPace - Inferior Greater Curvature Neuromuscular Stimulation Configuration |
| 3 | GastroPace - Pyloric Anturm Neuromuscular Stimulation Configuration |
| 4 | GastroPace - Pylorus Neuromuscular Stimulation Configuration |
| 5 | GastroPace - Pylorus and Pyloric Anturm Neuromuscular Stimulation Configuration |
| 6 | GastroPace - Pylorus and Anturm, Greater and Lessser Curvature Neuromuscular Stimulation Configuration |
| 7 | Nerve Cuff Electrode - Epineural Electrode Nerve Cuff Design |
| 8 | Nerve Cuff Electrode - Axial Electrode Blind End Port Design |
| 9 | Nerve Cuff Electrode - Axial Electrode Regeneration Port Design |
| 10 | Nerve Cuff Electrode - Axial Regeneration Tube Design |
| 11 | GastroPace - Neuromuscular Stimulation and Afferent Nerve Stimulation Configuration |
| 12 | GastroPace - Multichannel Neuromuscular Stimulation and Afferent Nerve Stimulation Configuration |
| 13 | Normal Thoracoabdominal anatomy |
| 14 | GastroPace - Efferent Multimodal Sympathetic Stimulation Configuration - Neuromodulatory Interfaces |
| 15 | GastroPace - Efferent Multimodal Sympathetic Stimulation Configuration - Neuromodulatory Interfaces, Connecting Cat |
| 16 | GastroPace - Multichannel Neuromuscular Stimulation and Multimodal Nerve Stimulation Configuration |
| 17 | Normal Spinal Cord Anatomy - Transverse Section |
| 18 | GastroPace - Spinal Cord Neuromodulatory Configuration |

|  |  | Figures | | | | | | | | | | | | | | | | | | |
|---|---|---|---|---|---|---|---|---|---|---|---|---|---|---|---|---|---|---|---|---|
| Label | Description | 1 | 2 | 3 | 4 | 5 | 6 | 7 | 8 | 9 | 10 | 11 | 12 | 13 | 14 | 15 | 16 | 17 | 18 | N |
| 1 | Implantable Pulse Generator | 1 | 1 | 1 | 1 | 1 | 1 |   |   |   |   | 1 | 1 |   |   |   | 1 |   |   |   |
| 2 | Electrode | 1 | 1 | 1 | 1 | 1 | 1 |   |   | 1 | 1 |   |   |   | 1 |   | 1 |   |   |   |
| 3 | Electrode | 1 | 1 | 1 | 1 | 1 | 1 |   |   |   |   | 1 | 1 |   |   |   | 1 |   |   |   |
| 4 | Attachment Fixture | 1 | 1 | 1 | 1 | 1 | 1 |   |   |   |   | 1 | 1 |   |   |   | 1 |   |   |   |
| 5 | Attachment Fixture | 1 | 1 | 1 | 1 | 1 | 1 |   |   |   |   | 1 | 1 |   |   |   | 1 |   |   |   |
| 6 | Attachment Means (suture/staple) | 1 | 1 | 1 | 1 | 1 | 1 |   |   |   |   | 1 | 1 |   |   |   | 1 |   |   |   |
| 7 | Attachment Means (suture/staple) | 1 | 1 | 1 | 1 | 1 | 1 |   |   |   |   | 1 | 1 |   |   |   | 1 |   |   |   |
| 8 | Stomach | 1 | 1 | 1 | 1 | 1 | 1 |   |   |   | 1 | 1 |   |   |   | 1 |   |   |   |   |
| 9 | Gastric Fundus | 1 | 1 | 1 | 1 | 1 | 1 |   |   |   |   | 1 | 1 |   |   |   |   |   |   |   |
| 10 | Greater Curvature of Stomach | 1 | 1 | 1 | 1 | 1 | 1 |   |   |   |   | 1 | 1 |   |   |   | 1 |   |   |   |
| 11 | Pyloric Antrum | 1 | 1 | 1 | 1 | 1 | 1 |   |   |   |   | 1 | 1 |   |   |   | 1 |   |   |   |
| 12 | Gastric Pylorus | 1 | 1 | 1 | 1 | 1 | 1 |   |   |   |   | 1 | 1 |   |   |   | 1 |   |   |   |
| 13 | Duodenum | 1 | 1 | 1 | 1 | 1 | 1 |   |   |   | 1 | 1 |   |   | 1 |   |   |   |   |   |
| 14 | Lower Esophageal Sphincter | 1 | 1 | 1 | 1 | 1 | 1 |   |   |   |   | 1 | 1 |   |   |   |   |   |   |   |
| 15 | Esophagus | 1 | 1 | 1 | 1 | 1 | 1 |   |   |   |   | 1 | 1 |   |   |   | 1 |   |   |   |
| 16 | Cardiac Notch of Stomach | 1 | 1 | 1 | 1 | 1 | 1 |   |   |   |   | 1 | 1 |   |   |   |   |   |   |   |
| 17 | Lesser Curvature of Stomach | 1 | 1 | 1 | 1 | 1 | 1 |   |   |   |   | 1 | 1 |   |   |   | 1 |   |   |   |
| 18 | Electrode Cable |   |   |   |   | 1 | 1 |   |   |   |   |   |   |   | 1 |   |   | 1 |   |   |
| 19 | Electrode Cable |   |   |   |   | 1 | 1 |   |   |   |   |   |   |   | 1 |   |   | 1 |   |   |
| 20 | Electrode Attachment Fixture |   |   |   |   | 1 | 1 |   |   |   |   |   |   |   | 1 |   |   | 1 |   |   |
| 21 | Electrode Attachment Fixture |   |   |   |   | 1 | 1 |   |   |   |   |   |   |   | 1 |   |   | 1 |   |   |
| 22 | Electrode Attachment Fixture |   |   |   |   | 1 | 1 |   |   |   |   |   |   |   | 1 |   |   | 1 |   |   |
| 23 | Electrode Attachment Fixture |   |   |   |   | 1 | 1 |   |   |   |   |   |   |   | 1 |   |   | 1 |   |   |
| 24 | Electrode |   |   |   |   |   | 1 |   |   |   |   |   |   |   | 1 |   |   | 1 |   |   |
| 25 | Electrode |   |   |   |   |   | 1 |   |   |   |   |   |   |   | 1 |   |   | 1 |   |   |
| 26 | Electrode |   |   |   |   |   | 1 |   |   |   |   |   |   |   | 1 |   |   | 1 |   |   |
| 27 | Electrode |   |   |   |   |   | 1 |   |   |   |   |   |   |   | 1 |   |   | 1 |   |   |
| 28 | Electrode |   |   |   |   |   | 1 |   |   |   |   |   |   |   | 1 |   |   | 1 |   |   |
| 29 | Electrode |   |   |   |   |   | 1 |   |   |   |   |   |   |   | 1 |   |   | 1 |   |   |
| 30 | Electrode |   |   |   |   |   | 1 |   |   |   |   |   |   |   | 1 |   |   | 1 |   |   |
| 31 | Electrode |   |   |   |   |   | 1 |   |   |   |   |   |   |   | 1 |   |   | 1 |   |   |
| 32 | Electrode Cable |   |   |   |   |   | 1 |   |   |   |   |   |   |   | 1 |   |   | 1 |   |   |
| 33 | Electrode Cable |   |   |   |   |   | 1 |   |   |   |   |   |   |   | 1 |   |   | 1 |   |   |
| 34 | Neuromodulatory interface ***** |   |   |   |   |   |   |   |   |   |   |   |   |   |   |   |   |   |   |   |
| 35 | Nerve |   |   |   |   |   |   | 1 | 1 | 1 | 1 |   |   |   |   |   |   |   |   |   |
| 36 | Nerve Cuff |   |   |   |   |   |   | 1 | 1 | 1 | 1 |   |   |   |   |   |   |   |   |   |
| 37 | Transected Nerve End |   |   |   |   |   |   | 1 | 1 | 1 | 1 |   |   |   |   |   |   |   |   |   |
| 38 | Longitudinal Electrode Array |   |   |   |   |   |   | 1 | 1 |   |   |   |   |   |   |   |   |   |   |   |
| 39 | Regeneration Port |   |   |   |   |   |   |   | 1 |   |   |   |   |   |   |   |   |   |   |   |
| 40 | Connecting Cable [=> connecting wire Array] |   |   |   |   |   |   | 1 | 1 |   |   |   |   |   |   |   |   |   |   |   |
| 41 | Nerve Cuff End Plate |   |   |   |   |   |   | 1 | 1 |   |   |   |   |   |   |   |   |   |   |   |
| 42 | Regeneration Tube Array |   |   |   |   |   |   |   |   | 1 |   |   |   |   |   |   |   |   |   |   |
| 43 | Regeneration Tube |   |   |   |   |   |   |   |   | 1 |   |   |   |   |   |   |   |   |   |   |
| 44 | Regeneration Electrode Array |   |   |   |   |   |   |   |   |   |   |   |   |   |   |   |   |   |   |   |
| 45 | Vagus Nerve Interface |   |   |   |   |   |   |   |   |   |   |   |   | 1 | 1 |   |   | 1 |   |   |
| 46 | Sympathetic Nerve Interface |   |   |   |   |   |   |   |   |   |   |   |   | 1 | 1 |   |   | 1 |   |   |
| 47 | Vagus Nerve |   |   |   |   |   |   |   |   |   |   |   |   | 1 | 1 |   |   | 1 |   |   |
| 48 | Sympathetic Nerve Branch |   |   |   |   |   |   |   |   |   |   |   |   | 1 | 1 |   |   | 1 |   |   |
| 49 | Epineural Electrode |   |   |   |   |   |   |   |   |   | 1 |   |   |   |   |   |   |   |   |   |
| 50 | Epineural Electrode |   |   |   |   |   |   |   |   |   | 1 |   |   |   |   |   |   |   |   |   |
| 51 | Epineural Electrode |   |   |   |   |   |   |   |   |   | 1 |   |   |   |   |   |   |   |   |   |
| 52 | Epineural Electrode Connecting Wire |   |   |   |   |   |   |   |   |   | 1 |   |   |   |   |   |   |   |   |   |
| 53 | Epineural Electrode Connecting Wire |   |   |   |   |   |   |   |   | 1 |   |   |   |   |   |   |   |   |   |   |
| 54 | Epineural Electrode Connecting Wire |   |   |   |   |   |   |   |   |   | 1 |   |   |   |   |   |   |   |   |   |
| 55 | Connecting Cable |   |   |   |   |   |   |   |   |   | 1 |   |   |   |   |   |   |   |   |   |
| 56 | Chest Wall |   |   |   |   |   |   |   |   |   |   |   |   | 1 | 1 | 1 | 1 |   |   |   |
| 57 | Aortic Arch |   |   |   |   |   |   |   |   |   |   |   |   | 1 | 1 | 1 | 1 |   |   |   |
| 58 | Thoracic Descending Aorta |   |   |   |   |   |   |   |   |   |   |   |   | 1 | 1 | 1 |   |   |   |   |
| 59 | Brachiocephalic Artery |   |   |   |   |   |   |   |   |   |   |   |   | 1 | 1 |   |   |   |   |   |
| 60 | Left Common Carotid Artery |   |   |   |   |   |   |   |   |   |   |   |   | 1 | 1 |   |   |   |   |   |
| 61 | Left Subclavian Artery |   |   |   |   |   |   |   |   |   |   |   |   | 1 | 1 |   |   |   |   |   |
| 62 | Abdominal Aorta |   |   |   |   |   |   |   |   |   |   |   |   | 1 | 1 |   |   |   |   |   |
| 63 | Trachea |   |   |   |   |   |   |   |   |   |   |   |   | 1 | 1 |   |   |   |   |   |
| 64 | Right Mainstem Bronchus |   |   |   |   |   |   |   |   |   |   |   |   | 1 | 1 |   |   |   |   |   |
| 65 | Left Mainstem Bronchus |   |   |   |   |   |   |   |   |   |   |   |   | 1 | 1 |   |   |   |   |   |
| 66 | Esophagus |   |   |   |   |   |   |   |   |   |   |   |   | 1 | 1 |   |   |   |   |   |
| 67 | Rib |   |   |   |   |   |   |   |   |   |   |   |   | 1 | 1 |   |   |   |   |   |
| 68 | Rib |   |   |   |   |   |   |   |   |   |   |   |   | 1 | 1 |   |   |   |   |   |
| 69 | Intercostal Nerve |   |   |   |   |   |   |   |   |   |   |   |   | 1 | 1 |   |   |   |   |   |
| 70 | Intercostal Nerve |   |   |   |   |   |   |   |   |   |   |   |   | 1 | 1 |   |   |   |   |   |
| 71 | Right Sympathetic Trunk |   |   |   |   |   |   |   |   |   |   |   |   | 1 | 1 | 1 | 1 |   |   |   |
| 72 | Left Sympathetic Trunk |   |   |   |   |   |   |   |   |   |   |   |   | 1 | 1 | 1 | 1 |   |   |   |
| 73 | Right Greater Splanchnic Nerve |   |   |   |   |   |   |   |   |   |   |   |   | 1 | 1 | 1 | 1 |   |   |   |
| 74 | Left Greater Splanchnic Nerve |   |   |   |   |   |   |   |   |   |   |   |   | 1 | 1 | 1 | 1 |   |   |   |
| 75 | Right Lesser Splanchnic Nerve |   |   |   |   |   |   |   |   |   |   |   |   | 1 | 1 | 1 | 1 |   |   |   |

-continued

| Label | Description | 1 | 2 | 3 | 4 | 5 | 6 | 7 | 8 | 9 | 10 | 11 | 12 | 13 | 14 | 15 | 16 | 17 | 18 | N |
|---|---|---|---|---|---|---|---|---|---|---|---|---|---|---|---|---|---|---|---|---|
| 76 | Left Lesser Splanchnic Nerve | | | | | | | | | | | | | 1 | 1 | 1 | 1 | | | |
| 77 | Diaphragm | | | | | | | | | | | | | 1 | 1 | 1 | 1 | | | |
| 78 | Right Subdiaphragmatic Greater Splanchnic Nerve | | | | | | | | | | | | | 1 | 1 | 1 | 1 | | | |
| 79 | Left Subdiaphragmatic Greater Splanchnic Nerve | | | | | | | | | | | | | 1 | 1 | 1 | 1 | | | |
| 80 | Right Subdiaphragmatic Lesser Splanchnic Nerve | | | | | | | | | | | | | 1 | 1 | 1 | 1 | | | |
| 81 | Left Subdiaphragmatic Lesser Splanchnic Nerve | | | | | | | | | | | | | 1 | 1 | 1 | 1 | | | |
| 82 | Mediastinum | | | | | | | | | | | | | 1 | 1 | 1 | 1 | | | |
| 83 | Sympathetic Trunk Neuromodulatory Interface | | | | | | | | | | | | | | 1 | 1 | 1 | | | |
| 84 | Sympathetic Trunk Neuromodulatory Interface | | | | | | | | | | | | | | 1 | 1 | 1 | | | |
| 85 | Sympathetic Trunk Neuromodulatory Interface | | | | | | | | | | | | | | 1 | 1 | 1 | | | |
| 86 | Sympathetic Trunk Neuromodulatory Interface | | | | | | | | | | | | | | 1 | 1 | 1 | | | |
| 87 | Thoracic Splanchnic Neuromodulatory Interface | | | | | | | | | | | | | | 1 | 1 | 1 | | | |
| 88 | Thoracic Splanchnic Neuromodulatory Interface | | | | | | | | | | | | | | 1 | 1 | 1 | | | |
| 89 | Thoracic Splanchnic Neuromodulatory Interface | | | | | | | | | | | | | | 1 | 1 | 1 | | | |
| 90 | Thoracic Splanchnic Neuromodulatory Interface | | | | | | | | | | | | | | 1 | 1 | 1 | | | |
| 91 | Abdominal Splanchnic Neuromodulatory Interface [Right Greater] | | | | | | | | | | | | | | 1 | 1 | 1 | | | |
| 92 | Abdominal Splanchnic Neuromodulatory Interface [Left Greater] | | | | | | | | | | | | | | 1 | 1 | 1 | | | |
| 93 | Abdominal Splanchnic Neuromodulatory Interface [Right Lesser] | | | | | | | | | | | | | | 1 | 1 | 1 | | | |
| 94 | Abdominal Splanchnic Neuromodulatory Interface [Left Lesser] | | | | | | | | | | | | | | 1 | 1 | 1 | | | |
| 95 | Right Vagus Nerve | | | | | | | | | | | | | 1 | 1 | 1 | 1 | | | |
| 96 | Left Vagus Nerve | | | | | | | | | | | | | 1 | 1 | 1 | 1 | | | |
| 97 | Vagus Neuromodulatory Interface | | | | | | | | | | | | | | 1 | 1 | 1 | | | |
| 98 | Vagus Neuromodulatory Interface | | | | | | | | | | | | | | 1 | 1 | 1 | | | |
| 99 | Implantable Pulse Generator | | | | | | | | | | | | | | | 1 | 1 | | | |
| 100 | Implantable Pulse Generator | | | | | | | | | | | | | | | 1 | 1 | | | |
| 101 | Implantable Pulse Generator | | | | | | | | | | | | | | | 1 | 1 | | | |
| 102 | Implantable Pulse Generator | | | | | | | | | | | | | | | 1 | 1 | | | |
| 103 | Connecting Cable [Right Sympathetic Trunk—Pre-Greater Spl] | | | | | | | | | | | | | | | 1 | 1 | | | |
| 104 | Connecting Cable [Left Sympathetic Trunk—Pre-Greater Spl] | | | | | | | | | | | | | | | 1 | 1 | | | |
| 105 | Connecting Cable [Rigth Sympathetic Trunk—Pre-Lesser Spl] | | | | | | | | | | | | | | | 1 | 1 | | | |
| 106 | Connecting Cable [Left Sympathetic Trunk—Pre-Lesser Spl] | | | | | | | | | | | | | | | 1 | 1 | | | |
| 107 | Connecting Cable [Right Greater Splanchnic—Thoracic] | | | | | | | | | | | | | | | 1 | 1 | | | |
| 108 | Connecting Cable [Left Greater Splanchnic—Thoracic] | | | | | | | | | | | | | | | 1 | 1 | | | |
| 109 | Connecting Cable [Right Lesser Splanchnic—Thoracic] | | | | | | | | | | | | | | | 1 | 1 | | | |
| 110 | Connecting Cable [Left Lesser Splanchnic—Thoracic] | | | | | | | | | | | | | | | 1 | 1 | | | |
| 111 | Connecting Cable [Right Greater Splanchnic] | | | | | | | | | | | | | | | 1 | 1 | | | |
| 112 | Connecting Cable [Left Greater Splanchnic] | | | | | | | | | | | | | | | 1 | 1 | | | |
| 113 | Connecting Cable [Right Lesser Splanchnic] | | | | | | | | | | | | | | | 1 | 1 | | | |
| 114 | Connecting Cable [Left Lesser Splanchnic] | | | | | | | | | | | | | | | 1 | 1 | | | |
| 115 | Connecting Cable [Rigth Vagus] | | | | | | | | | | | | | | | 1 | 1 | | | |
| 116 | Connecting Cable [Left Vagus] | | | | | | | | | | | | | | | 1 | 1 | | | |
| 117 | Epineural Cuff Electrode Neuromodulatory Interface | | | | | | | | | | | | | | | | | | | |
| 118 | Longitudinal Electrode Neuromodulatory Interface | | | | | | | | | | | | | | | | | | | |
| 119 | Longitudinal Electrode Regeneration Port Neuromodulatory Interface | | | | | | | | | | | | | | | | | | | |
| 120 | Regeneration Tube Neuromodulatory Interface | | | | | | | | | | | | | | | | | | | |
| 121 | Intermediolateral Nucleus | | | | | | | | | | | | | | | | | 1 | 1 | |
| 122 | Spinal Cord White Matter | | | | | | | | | | | | | | | | | 1 | 1 | |
| 123 | Anterior Median Fissure | | | | | | | | | | | | | | | | | 1 | | |
| 124 | Ventral Spinal Root | | | | | | | | | | | | | | | | | 1 | 1 | |
| 125 | Dorsal Spinal Root | | | | | | | | | | | | | | | | | 1 | 1 | |
| 126 | Spinal Ganglion | | | | | | | | | | | | | | | | | 1 | 1 | |
| 127 | Spinal Nerve | | | | | | | | | | | | | | | | | 1 | 1 | |
| 128 | Spinal Nerve Anterior Ramus | | | | | | | | | | | | | | | | | 1 | 1 | |
| 129 | Spinal Nerve Posterior Ramus | | | | | | | | | | | | | | | | | 1 | 1 | |
| 130 | Grey Ramus Communicantes | | | | | | | | | | | | | | | | | 1 | 1 | |
| 131 | White Ramus Communicantes | | | | | | | | | | | | | | | | | 1 | 1 | |
| 132 | Sympathetic Trunk | | | | | | | | | | | | | | | | | 1 | 1 | |
| 133 | Pia mater | | | | | | | | | | | | | | | | | 1 | | |
| 134 | Subarachnoid Space | | | | | | | | | | | | | | | | | 1 | 1 | |
| 135 | Arachnoid | | | | | | | | | | | | | | | | | 1 | | |
| 136 | Meningeal Layer of Dura Mater | | | | | | | | | | | | | | | | | 1 | 1 | |
| 137 | Epidural Space | | | | | | | | | | | | | | | | | 1 | 1 | |

-continued

| Label | Description | 1 | 2 | 3 | 4 | 5 | 6 | 7 | 8 | 9 | 10 | 11 | 12 | 13 | 14 | 15 | 16 | 17 | 18 | N |
|---|---|---|---|---|---|---|---|---|---|---|---|---|---|---|---|---|---|---|---|---|
| 138 | Periostial Layer of Dura Mater | | | | | | | | | | | | | | | | | 1 | 1 | |
| 139 | Vertebral Spinous Process | | | | | | | | | | | | | | | | | 1 | 1 | |
| 140 | Vertebral Facet | | | | | | | | | | | | | | | | | 1 | | |
| 141 | Ventral Horn of Spinal Gray Matter | | | | | | | | | | | | | | | | | 1 | | |
| 142 | Dorsal Horn of Spinal Gray Matter | | | | | | | | | | | | | | | | | 1 | | |
| 143 | Anterior Central Spinal Neuromodulatory Interface | | | | | | | | | | | | | | | | | | 1 | |
| 144 | Anterial Right Lateral Spinal Neuromodulatory Interface | | | | | | | | | | | | | | | | | | 1 | |
| 145 | Anterial Left Lateral Spinal Neuromodulatory Interface | | | | | | | | | | | | | | | | | | 1 | |
| 146 | Posterior Central Spinal Neuromodulatory Interface | | | | | | | | | | | | | | | | | | 1 | |
| 147 | Posterior Right Lateral Spinal Neuromodulatory Interface | | | | | | | | | | | | | | | | | | 1 | |
| 148 | Posterior Left Lateral Spinal Neuromodulatory Interface | | | | | | | | | | | | | | | | | | 1 | |
| 149 | Right Lateral Spinal Neuromodulatory Interface | | | | | | | | | | | | | | | | | | 1 | |
| 150 | Left Lateral Spinal Neuromodulatory Interface | | | | | | | | | | | | | | | | | | 1 | |
| 151 | Spinal Cord | | | | | | | | | | | | | | | | | 1 | 1 | |
| 152 | Intermediolateral Nucleus Neuromodulatory Interface | | | | | | | | | | | | | | | | | | 1 | |

The invention claimed is:

1. A method for treating a medical condition comprising:
   modulating the sympathetic nervous system, said modulating comprising delivering a signal using a neuromodulator which activates the splanchnic nerve to induce weight loss.

2. The method recited in claim 1, wherein said activating the splanchnic nerve induces weight loss by reducing appetite.

3. The method recited in claim 2, wherein said activating the splanchnic nerve induces weight loss by increasing energy expenditure.

4. The method recited in claim 1 wherein said activating comprises activating the splanchnic nerve and inducing physiologic effects of splanchnic stimulation.

5. The method recited in claim 1 wherein said activating the splanchnic nerve induces weight loss by inducing satiety.

6. The method recited in claim 5 wherein said activating increases pyloric sphincter tone.

7. The method recited in claim 6 wherein said increased pyloric sphincter tone carries out the physiologic function of the pylorus, namely decreased gastric emptying.

8. A method for treating a medical condition comprising:
   modulating the sympathetic nervous system, said modulating comprising delivering a signal using a neuromodulator to activate a splanchnic nerve, said splanchnic nerve comprising at least one of the superior splanchnic nerve, inferior splanchnic nerve, and other neural structure, said activating inducing physiological effects, and
   wherein said physiologic effects include change in plasma glucose levels.

9. A method for treating a medical condition comprising:
   modulating the sympathetic nervous system, said modulating comprising delivering a signal using a neuromodulator to activate a splanchnic nerve, said splanchnic nerve comprising at least one of the superior splanchnic nerve, inferior splanchnic nerve, and other neural structure, said activating inducing physiological effects, and
   wherein said physiologic effects include change in plasma insulin levels.

10. A method for treating a medical condition comprising:
    modulating the sympathetic nervous system, said modulating comprising delivering a signal using a neuromodulator to activate a splanchnic nerve, said splanchnic nerve comprising at least one of the superior splanchnic nerve, inferior splanchnic nerve, and other neural structure, said activating inducing physiological effects, and
    wherein said physiologic effects include change in appetite.

11. A method for treating a medical condition comprising:
    modulating the sympathetic nervous system, said modulating comprising delivering a signal to activate a splanchnic nerve, said splanchnic nerve comprising at least one of the superior splanchnic nerve, inferior splanchnic nerve, and other neural structure, and
    wherein said activating the splanchnic nerve comprises:
    activating the splanchnic nerve to increase plasma glucose levels, thereby reducing appetite; and
    activating the splanchnic nerve to increase plasma catecholamine levels, thereby increasing energy expenditure.

12. A method for treating a medical condition comprising:
    modulating the sympathetic nervous system, said modulating comprising delivering a signal using a neuromodulator to activate a splanchnic nerve to reduce insulin secretion.

13. A method for activating the splanchnic nerve to treat obesity comprising:
    applying a current pulse to the splanchnic nerve, and
    selecting the duration of said current pulse to be no greater than the chronaxie of the splanchnic nerve.

14. A method for activating the splanchnic nerve to treat obesity comprising:
    applying a current pulse to the splanchnic nerve, and
    selecting the duration of said current pulse to be within the range of 1 microsecond and 500 milliseconds.

15. A method for activating the splanchnic nerve to treat obesity comprising:

applying a current pulse to the splanchnic nerve, wherein said current pulse is biphasic.

16. A method for activating the splanchnic nerve to treat obesity comprising:
applying a current pulse to the splanchnic nerve, and
selecting the amplitude of said current pulse to be within the range of 1 microamp and 1000 milliamps.

17. A method for activating the splanchnic nerve to treat obesity comprising:
applying a current pulse to the splanchnic nerve, and
selecting the interpulse interval to be within the range of 1 microsecond and 1000 milliseconds.

18. A method for activating the splanchnic nerve to treat obesity comprising:
applying a current pulse to the splanchnic nerve, and
selecting the duration of said current pulse to be between 100 microseconds and 400 microseconds.

19. A method for activating the splanchnic nerve to treat obesity comprising:
implanting a pulse generator within a patient, said pulse generator having programmable treatment parameters,
programming said treatment parameters to induce satiety, and
applying a current pulse to the splanchnic nerve with said pulse generator.

20. A method for treating a medical condition comprising:
modulating the sympathetic nervous system to treat obesity, wherein obesity is treated using unipolar stimulation of a splanchnic nerve.

21. The method recited in claim 20, further comprising:
placing a first electrode in general proximity to the splanchnic nerve; and
applying a sufficiently large energy field to stimulate the splanchnic nerve in general proximity to said first electrode.

22. The method recited in claim 20, further comprising:
placing a first electrode in general proximity to the splanchnic nerve; and
applying a sufficiently large energy field with said first electrode to electrically couple with a second electrode remote from said first electrode, said energy field being sufficiently large to stimulate the splanchnic nerve in general proximity to said first electrode.

23. The method as recited in claim 22, further comprising implanting a pulse generator within a patient.

24. The method as recited in claim 22, further comprising:
implanting a pulse generator within a patient, remote from said splanchnic nerve, said pulse generator having an external portion adapted to function as said remote second electrode; and
applying a current pulse to said first electrode with said pulse generator, said current pulse being sufficiently large to electrically couple said first electrode with said external portion of said pulse generator.

25. The method recited in claim 24, further comprising providing a housing on said pulse generator adapted to function as said second electrode.

26. A method for treating a medical condition comprising:
modulating the sympathetic nervous system to treat obesity, wherein obesity is treated using bipolar stimulation of a splanchnic nerve.

27. A method for treating a user comprising delivering energy using a neuromodulator in communication with at least a portion of the intermediolateral nucleus at levels T1-T9.

28. The method of claim 27 wherein said neuromodulator is in communication with at least a portion of the intermediolateral nucleus at levels T6-T9.

29. The method of claim 27 wherein said neuromodulator is in communication with at least a portion of the intermediolateral nucleus at levels T1.

30. The method of claim 27 wherein said neuromodulator is in communication with at least a portion of the intermediolateral nucleus at levels T2.

31. The method of claim 27 wherein said neuromodulator is in communication with at least a portion of the intermediolateral nucleus at levels T3.

32. The method of claim 27 wherein said neuromodulator is in communication with at least a portion of the intermediolateral nucleus at levels T4.

33. The method of claim 27 wherein said neuromodulator is in communication with at least a portion of the intermediolateral nucleus at levels T5.

34. The method of claim 27 wherein said neuromodulator is in communication with at least a portion of the intermediolateral nucleus at levels T6.

35. The method of claim 27 wherein said neuromodulator is in communication with at least a portion of the intermediolateral nucleus at levels T7.

36. The method of claim 27 wherein said neuromodulator is in communication with at least a portion of the intermediolateral nucleus at levels T8.

37. The method of claim 27 wherein said neuromodulator is in communication with at least a portion of the intermediolateral nucleus at levels T9.

38. A method for treating a user comprising delivering energy using a neuromodulator in communication with projections from the intermediolateral nucleus at levels T1-T9.

39. The method of claim 38 wherein said neuromodulator is in communication with projections from the intermediolateral nucleus at levels T6-T9.

40. The method of claim 38 wherein said neuromodulator is in communication with projections from the intermediolateral nucleus at levels T1.

41. The method of claim 38 wherein said neuromodulator is in communication with projections from the intermediolateral nucleus at levels T2.

42. The method of claim 38 wherein said neuromodulator is in communication with projections from the intermediolateral nucleus at levels T3.

43. The method of claim 38 wherein said neuromodulator is in communication with projections from the intermediolateral nucleus at levels T4.

44. The method of claim 38 wherein said neuromodulator is in communication with projections from the intermediolateral nucleus at levels T5.

45. The method of claim 38 wherein said neuromodulator is in communication with projections from the intermediolateral nucleus at levels T6.

46. The method of claim 38 wherein said neuromodulator is in communication with projections from the intermediolateral nucleus at levels T7.

47. The method of claim 38 wherein said neuromodulator is in communication with projections from the intermediolateral nucleus at levels T8.

48. The method of claim 38 wherein said neuromodulator is in communication with projections from the intermediolateral nucleus at levels T9.

49. A method for treating a user comprising delivering energy using a neuromodulator in communication with projections to the intermediolateral nucleus.

50. The method of claim 49 wherein said neuromodulator is in communication with projections to the intermediolateral nucleus at levels T6-T9.

51. The method of claim 49 wherein said neuromodulator is in communication with projections to the intermediolateral nucleus at levels T1.

52. The method of claim 49 wherein said neuromodulator is in communication wit projections to the intermediolateral nucleus at levels T2.

53. The method of claim 49 wherein said neuromodulator is in communication with projections to the intermediolateral nucleus at levels T3.

54. The method of claim 49 wherein said neuromodulator is in communication with projections to the intermediolateral nucleus at levels T4.

55. The method of claim 49 wherein said neuromodulator is in communication with projections to the intermediolateral nucleus at levels T5.

56. The method of claim 49 wherein said neuromodulator is in communication with projections to the intermediolateral nucleus at levels T6.

57. The method of claim 49 wherein said neuromodulator is in communication with projections to the intermediolateral nucleus at levels T7.

58. The method of claim 49 wherein said neuromodulator is in communication with projections to the intermediolateral nucleus at levels T8.

59. The method of claim 49 wherein said neuromodulator is in communication with projections to the intermediolateral nucleus at levels T9.

60. The method of claim 49 wherein said neuromodulator is in communication with projections to the intermediolateral nucleus at levels T10.

61. The method of claim 49 wherein said neuromodulator is in communication with projections to the intermediolateral nucleus at levels T11.

62. The method of claim 49 wherein said neuromodulator is in communication with projections to the intermediolateral nucleus at levels T12.

63. The method of claim 49 wherein said neuromodulator is in communication with projections to the intermediolateral nucleus at levels C1.

64. The method of claim 49 wherein said neuromodulator is in communication with projections to the intermediolateral nucleus at levels C2.

65. The method of claim 49 wherein said neuromodulator is in communication with projections to the intermediolateral nucleus at levels C3.

66. The method of claim 49 wherein said neuromodulator is in communication with projections to the intermediolateral nucleus at levels C4.

67. The method of claim 49 wherein said neuromodulator is in communication with projections to the intermediolateral nucleus at levels C5.

68. The method of claim 49 wherein said neuromodulator is in communication with projections to the intermediolateral nucleus at levels C6.

69. The method of claim 49 wherein said neuromodulator is in communication with projections to the intermediolateral nucleus at levels C7.

70. The method of claim 49 wherein said neuromodulator is in communication with projections to the intermediolateral nucleus at levels C8.

71. The method of claim 49 wherein said neuromodulator is in communication with projections to the intermediolateral nucleus at levels L1.

72. The method of claim 49 wherein said neuromodulator is in communication with projections to the intermediolateral nucleus at levels L2.

73. The method of claim 49 wherein said neuromodulator is in communication with projections to the intermediolateral nucleus at levels L3.

74. The method of claim 49 wherein said neuromodulator is in communication with projections to the intermediolateral nucleus at levels L4.

75. The method of claim 49 wherein said neuromodulator is in communication with projections to the intermediolateral nucleus at levels L5.

76. The method of claim 49 wherein said neuromodulator is in communication with projections to the intermediolateral nucleus at levels S1.

77. The method of claim 49 wherein said neuromodulator is in communication with projections to the intermediolateral nucleus at levels S2.

78. The method of claim 49 wherein said neuromodulator is in communication with projections to the intermediolateral nucleus at levels S3.

79. The method of claim 49 wherein said neuromodulator is in communication with projections to the intermediolateral nucleus at levels S4.

80. The method of claim 49 wherein said neuromodulator is in communication with projections to the intermediolateral nucleus at levels S5.

81. A method for treating a user comprising applying an electrical signal to the intermediolateral nucleus, wherein duration of said signal is greater than 10 seconds per day.

82. The method of claim 81, wherein duration of said signal is greater than 20 seconds per day.

83. The method of claim 81, wherein duration of said signal is greater than 30 seconds per day.

84. The method of claim 81, wherein duration of said signal is greater than 1 minute per day.

85. The method of claim 81, wherein duration of said signal is greater than 2 minutes per day.

86. The method of claim 81, wherein duration of said signal is greater than 5 minutes per day.

87. The method of claim 81, wherein duration of said signal is greater than 7 minutes per day.

88. The method of claim 81, wherein duration of said signal is greater than 10 minutes per day.

89. The method of claim 81, wherein duration of said signal is greater than 12 minutes per day.

90. The method of claim 81, wherein duration of said signal is greater than 15 minutes per day.

91. The method of claim 81, wherein duration of said signal is greater than 20 minute per day.

92. The method of claim 81, wherein duration of said signal is greater than 30 minutes per day.

93. The method of claim 81, wherein duration of said signal is greater than 45 minutes per day.

94. The method of claim 81, wherein duration of said signal is greater than 1 hour per day.

95. The method of claim 81, wherein duration of said signal is greater than 2 hours per day.

96. The method of claim 81, wherein duration of said signal is greater than 4 hour per day.

97. The method of claim 81, wherein duration of said signal is greater than 8 hour per day.

98. The method of claim 81, wherein duration of said signal is greater than 12 hour per day.

99. The method of claim 81, wherein said signal is continuous.

100. The method of claim 81, wherein said signal is intermittent.

101. The method of claim 81, wherein said signal is applied at regular intervals.

102. A method for activating the intermediolateral nucleus to treat a user comprising:
applying an electrical signal to the intermediolateral nucleus; and
selecting stimulation parameters which cause weight reduction.

103. A method for activating the intermediolateral nucleus to treat a user comprising:
applying an electrical signal to the intermediolateral nucleus; and
selecting stimulation parameters which cause appetite reduction.

104. A method for activating the intermediolateral nucleus to treat a user comprising:
applying an electrical signal to the intermediolateral nucleus; and
selecting stimulation parameters which induce satiety.

105. A method for activating the intermediolateral nucleus to treat a user comprising:
applying an electrical signal to the intermediolateral nucleus; and
selecting stimulation parameters which cause increase in metabolism.

106. A method for activating the intermediolateral nucleus to treat a user comprising:
selecting a user in whom body weight is to be reduced; and
applying an electrical signal to the intermediolateral nucleus.

107. The method of claim 106 wherein said body weight is above a desired weight.

108. The method of claim 106 wherein said user has a body weight which is in the obese range.

109. A method for activating the intermediolateral nucleus to treat a user comprising:
selecting a user with a body weight above normal; and
applying an electrical signal to the intermediolateral nucleus.

110. The method of claim 109 wherein said body weight is substantially above normal.

111. The method of claim 109 wherein said user is obese.

112. The method of claim 109 wherein said user is morbidly obese.

113. A method for activating the intermediolateral nucleus to treat obesity as in any one of claims 27, 38, 49, 81, 84, 102, 103, 104, 105, 106, 109, or 111 further comprising:
applying an electrical signal to the intermediolateral nucleus, and
selecting the duration of said electrical signal to be no greater than the chronaxie of the intermediolateral nucleus.

114. A method for activating the intermediolateral nucleus to treat obesity as in any one of claims 27, 38, 49, 81, 84, 102, 103, 104, 105, 106, 109, or 111 further comprising:
applying an electrical signal to the intermediolateral nucleus, and
selecting the duration of said electrical signal to be within the range of 1 microsecond and 1000 milliseconds.

115. A method for activating the intermediolateral nucleus to treat obesity as in any one of claims 27, 38, 49, 81, 84, 102, 103, 104, 105, 106, 109, or 111 further comprising:
Applying an electrical signal to the intermediolateral nucleus, wherein said electrical signal is biphasic.

116. A method for activating the intermediolateral nucleus to treat obesity as in any one of claims 27, 38, 49, 81, 84, 102, 103, 104, 105, 106, 109, or 111 further comprising:
applying an electrical signal to the intermediolateral nucleus, and
selecting the amplitude of said electrical signal to be within the range of 1 microamp and 1000 milliamps.

117. A method for activating the intermediolateral nucleus to treat obesity as in any one of claims 27, 38, 49, 81, 84, 102, 103, 104, 105, 106, 109, or 111 further comprising:
applying an electrical signal to the intermediolateral nucleus, and
selecting the interpulse interval to be within the range of 1 microsecond and 1000 milliseconds.

118. A method for activating the intermediolateral nucleus to treat obesity as in any one of claims 27, 38, 49, 81, 84, 102, 103, 104, 105, 106, 109, or 111 further comprising:
applying an electrical signal to the intermediolateral nucleus, and
selecting the duration of said electrical signal to be between 100 microseconds and 400 microseconds.

119. A method for activating the intermediolateral nucleus to treat obesity as in any one of claims 27, 38, 49, 81, 84, 102, 103, 104, 105, 106, 109, or 111 further comprising:
implanting a pulse generator within a patient, said pulse generator having programmable treatment parameters,
programming said treatment parameters to induce satiety, and
applying an electrical signal to the intermediolateral nucleus with said pulse generator.

120. A method for treating a medical condition as in any one of claims 27, 38, 49, 81, 84, 102, 103, 104, 105, 106, 109, or 111 further comprising:
modulating the sympathetic nervous system to treat obesity, wherein obesity is treated using unipolar stimulation of an intermediolateral nucleus.

121. A method for treating a medical condition as in any one of claims 27, 38, 49, 81, 84, 102, 103, 104, 105, 106, 109, or 111 further comprising:
modulating the sympathetic nervous system to treat obesity, wherein obesity is treated using bipolar stimulation of an intermediolateral nucleus.

122. A method for treating a medical condition as in any one of claims 27, 38, 49, 81, 84, 102, 103, 104, 105, 106, 109, or 111 further comprising:
modulating the sympathetic nervous system to treat obesity, wherein obesity is treated using unipolar stimulation of an intermediolateral nucleus.

123. A method for treating a medical condition as in any one of claims 27, 38, 49, 81, 84, 102, 103, 104, 105, 106, 109, or 111 further comprising:
modulating the sympathetic nervous system to treat obesity, wherein obesity is treated using unipolar stimulation of an intermediolateral nucleus;
placing a first electrode in general proximity to the intermediolateral nucleus; and
applying a sufficiently large energy field to stimulate the intermediolateral nucleus in general proximity to said first electrode.

124. A method for treating a medical condition as in any one of claims 27, 38, 49, 81, 84, 102, 103, 104, 105, 106, 109, or 111 further comprising:
modulating the sympathetic nervous system to treat obesity, wherein obesity is treated using unipolar stimulation of an intermediolateral nucleus;
placing a first electrode in general proximity to the intermediolateral nucleus; and applying a sufficiently large energy field with said first electrode to electrically couple with a second electrode remote from said first electrode, said energy field being sufficiently large to stimulate the intermediolateral nucleus in general proximity to said first electrode.

125. A method for treating a medical condition as in any one of claims 27, 38, 49, 81, 84, 102, 103, 104, 105, 106, 109, or 111 further comprising:
    modulating the sympathetic nervous system to treat obesity, wherein obesity is treated using unipolar stimulation of an intermediolateral nucleus;
    placing a first electrode in general proximity to the intermediolateral nucleus;
    applying a sufficiently large energy field with said first electrode to electrically couple with a second electrode remote from said first electrode, said energy field being sufficiently large to stimulate the intermediolateral nucleus in general proximity to said first electrode; and
    implanting a pulse generator within a patient.

126. A method for treating a medical condition as in any one of claims 27, 38, 49, 81, 84, 102, 103, 104, 105, 106, 109, or 111 further comprising:
    modulating the sympathetic nervous system to treat obesity, wherein obesity is treated using unipolar stimulation of an intermediolateral nucleus;
    placing a first electrode in general proximity to the intermediolateral nucleus; and
    applying a sufficiently large energy field with said first electrode to electrically couple with a second electrode remote from said first electrode, said energy field being sufficiently large to stimulate the intermediolateral nucleus in general proximity to said first electrode; and
    implanting a pulse generator within a patient, remote from said intermediolateral nucleus, said pulse generator having an external portion adapted to function as said remote second electrode; and
    applying an electrical signal to said first electrode with said pulse generator, said electrical signal being sufficiently large to electrically couple said first electrode with said external portion of said pulse generator.

127. A method for treating a medical condition as in any one of claims 27, 38, 49, 81, 84, 102, 103, 104, 105, 106, 109, or 111 further comprising:
    modulating the sympathetic nervous system to treat obesity, wherein obesity is treated using unipolar stimulation of an intermediolateral nucleus;
    placing a first electrode in general proximity to the intermediolateral nucleus; and
    applying a sufficiently large energy field with said first electrode to electrically couple with a second electrode remote from said first electrode, said energy field being sufficiently large to stimulate the intermediolateral nucleus in general proximity to said first electrode; and
    implanting a pulse generator within a patient, remote from said intermediolateral nucleus, said pulse generator having an external portion adapted to function as said remote second electrode; and
    applying an electrical signal to said first electrode with said pulse generator, said electrical signal being sufficiently large to electrically couple said first electrode with said external portion of said pulse generator; and
    providing a housing on said pulse generator adapted to function as said second electrode.

128. The method recited in claims 27, 38, 49, 81, 84, 102, 103, 104, 105, 106, 109, or 111, further comprising implanting at least one electrode adjacent to the spinal cord.

129. The method recited in claims 27, 38, 49, 81, 84, 102, 103, 104, 105, 106, 109, or 111, further comprising implanting at least one electrode within the spinal canal.

130. The method recited in claims 27, 38, 49, 81, 84, 102, 103, 104, 105, 106, 109, or 111, further comprising implanting at least one electrode adjacent to the lateral surface of the spinal cord.

131. The method recited in claims 27, 38, 49, 81, 84, 102, 103, 104, 105, 106, 109, or 111, further comprising implanting at least one electrode along the lateral surface of the spinal cord.

132. The method recited in claims 27, 38, 49, 81, 84, 102, 103, 104, 105, 106, 109, or 111, further comprising implanting at least one electrode adjacent to the dorsolateral surface of the spinal cord.

133. The method recited in claims 27, 38, 49, 81, 84, 102, 103, 104, 105, 106, 109, or 111, further comprising implanting at least one electrode adjacent to the ventrolateral surface of the spinal cord.

134. The method recited in claims 27, 38, 49, 81, 84, 102, 103, 104, 105, 106, 109, or 111, further comprising implanting at least one electrode such that it is in communication with the spinal cord.

135. The method recited in claims 27, 38, 49, 81, 84, 102, 103, 104, 105, 106, 109, or 111, further comprising implanting at least one electrode such that it is in communication with the lateral portion of the spinal grey matter.

136. The method recited in claims 27, 38, 49, 81, 84, 102, 103, 104, 105, 106, 109, or 111, further comprising implanting at least one electrode such that it is in communication with the dorsolateral portion of the spinal grey matter.

137. The method recited in claims 27, 38, 49, 81, 84, 102, 103, 104, 105, 106, 109, or 111, further comprising implanting at least one electrode such that it is in communication with the ventrolateral portion of the spinal greay matter.

138. The method recited in claims 27, 38, 49, 81, 84, 102, 103, 104, 105, 106, 109, or 111, further comprising implanting at least one electrode such that it is in communication with the intermediolateral nucleus.

139. The method recited in claims 27, 38, 49, 81, 84, 102, 103, 104, 105, 106, 109, or 111, further comprising implanting at least one electrode such that it is in communication with projections from the intermediolateral nucleus.

140. The method recited in any one of claims 41-53, further comprising implanting at least one electrode such that it is in communication with projections to the intermediolateral nucleus.

141. The method recited in claim 139, wherein said projection comprises a splanchnic nerve.

142. The method recited in claim 139, wherein said projections project to abdominal organs.

143. The method recited in claim 139, wherein said projections modulate metabolism.

144. The method recited in claim 139, wherein said projections project to abdominal organisms to modulate metabolism.

145. The method recited in claim 139, wherein said projections arise from thoracic spinal segments.

146. The method recited in claim 142, wherein said projections arise from spinal segments T6-T9.

147. The method recited in claim 142, wherein said projections arise from spinal segment T6.

148. The method recited in claim 142, wherein said projections arise from spinal segment T7.

149. The method recited in claim 142, wherein said projections arise from spinal segment T8.

150. The method recited in claim 142, wherein said projections arise from spinal segment T9.

151. The method recited in claim 143, wherein said projections arise from spinal segments T6-T9.

152. The method recited in claim 143, wherein said projections arise from spinal segment T6.

153. The method recited in claim 143, wherein said projections arise from spinal segment T7.

154. The method recited in claim 143, wherein said projections arise from spinal segment T8.

155. The method recited in claim 143, wherein said projections arise from spinal segment T9.

156. The method recited in claim 140, wherein said projection comprises a splanchnic nerve.

157. The method recited in claim 140, wherein said projections arise from abdominal organs.

158. The method recited in any one of claims 27, 38, 49, 81, 84, 102, 103, 104, 105, 106, 109, or 111, further comprising:
   A. implanting at least one electrode such that it is in communication with projections to the intermediolateral nucleus; and
   B. implanting at least one electrode such that it is in communication with projections from the intermediolateral nucleus.

159. The method recited in any one of claims 27, 38, 49, 81, 84, 102, 103, 104, 105, 106, 109, or 111, further comprising:
   A. implanting at least one electrode such that it is in communication with afferent pathways comprising the intermediolateral nucleus; and
   B. implanting at least one electrode such that is it in communication with efferent pathways comprising the intermediolateral nucleus.

160. The method recited in any one of claims 27, 38, 49, 81, 84, 102, 103, 104, 105, 106, 109, or 111, further comprising:
   A. implanting at least one electrode such that it is in communication with afferent pathways comprising the spinal cord; and
   B. implanting at least one electrode such that it is in communication with efferent pathways comprising the intermediolateral nucleus.

161. The method recited in claims any one of 41-53, further comprising:
   A. implanting at least one electrode such that it is in communication with afferent pathways comprising the intermediolateral nucleus; and
   B. implanting at least one electrode such that it is in communication with efferent pathways comprising the spinal cord.

162. The method as in claim 27, wherein said energy is an electrical signal.

163. The method as in claim 38, wherein said energy is an electrical signal.

164. The method as in claim 49, wherein said energy is an electrical signal.

165. The method as in any one of claims 81, 84, 102, 103, 104, 105, 106, 109, or 111, 162, 163, 164, wherein said electrical signal is monopolar.

166. The method as in any one of claims 81, 84, 102, 103, 104, 105, 106, 109, or 111, 162, 163, 164, wherein said electrical signal is bipolar.

167. The method as in any one of claims 81, 84, 102, 103, 104, 105, 106, 109, or 111, 162, 163, 164, wherein said electrical signal is bipolar pulse pair.

168. The method as in any one of claims 81, 84, 102, 103, 104, 105, 106, 109, or 111, 162, 163, 164, wherein said electrical signal is bipolar pulse pair with an interpulse interval.

169. The method as in any one of claims 81, 84, 102, 103, 104, 105, 106, 109, or 111, 162, 163, 164, wherein said electrical signal is charge balanced.

170. The method as in any one of claims 81, 84, 102, 103, 104, 105, 106, 109, or 111, 162, 163, 164, wherein said signal is single channel.

171. The method as in any one of claims 81, 84, 102, 103, 104, 105, 106, 109, or 111, 162, 163, 164, wherein said signal is multichannel.

172. The method as in any one of claims 81, 84, 102, 103, 104, 105, 106, 109, or 111, 162, 163, 164, wherein said signal comprises a frequency within the range of 0.1 Hertz to 1000 Hertz.

173. The method as in any one of claims 81, 84, 102, 103, 104, 105, 106, 109, or 111, 162, 163, 164, wherein said signal comprises a frequency greater than 100 Hertz.

174. The method as in any one of claims 81, 84, 102, 103, 104, 105, 106, 109, or 111, 162, 163, 164, wherein said signal comprises a frequency within the range of 50 to 100 Hertz.

175. The method as in any one of claims 81, 84, 102, 103, 104, 105, 106, 109, or 111, 162, 163, 164, wherein said signal comprises a frequency within the range of 10 to 50 Hertz.

176. The method as in any one of claims 81, 84, 102, 103, 104, 105, 106, 109, or 111, 162, 163, 164, wherein said signal comprises a frequency within the range of 0.1 to 10 Hertz.

177. The method as in any one of claims 81, 84, 102, 103, 104, 105, 106, 109, or 111, 162, 163, 164, wherein said signal comprises a frequency less than 5 Hertz.

178. The method as in any one of claims 81, 84, 102, 103, 104, 105, 106, 109, or 111, 162, 163, 164, wherein said signal comprises a pulse width within the range of 1 microsecond to 500 milliseconds.

179. The method as in any one of claims 81, 84, 102, 103, 104, 105, 106, 109, or 111, 162, 163, 164, wherein said signal comprises an interpulse interval within the range of 1 microseconds to 1000 milliseconds.

180. The method as in any one of claims 81, 84, 102, 103, 104, 105, 106, 109, or 111, 162, 163, 164, wherein said signal is a pulse pair.

181. The method as in any one of claims 81, 84, 102, 103, 104, 105, 106, 109, or 111, 162, 163, 164, wherein said signal is biphasic.

182. The method as in any one of claims 81, 84, 102, 103, 104, 105, 106, 109, or 111, 162, 163, 164, wherein said electrical signal is a current pulse.

183. The method as in any one of claims 81, 84, 102, 103, 104, 105, 106, 109, or 111, 162, 163, 164, wherein said electrical signal is current regulated.

184. The method as in any one of claims 81, 84, 102, 103, 104, 105, 106, 109, or 111, 162, 163, 164, wherein said electrical signal comprises a current amplitude within the range of 1 microamp to 1000 milliamps.

185. The method as in any one of claims 81, 84, 102, 103, 104, 105, 106, 109, or 111, 162, 163, 164, wherein said electrical signal comprises a current amplitude within the range of 0.1 milliamp to 50 milliamps.

186. The method as in any one of claims 81, 84, 102, 103, 104, 105, 106, 109, or 111, 162, 163, 164, wherein said electrical signal is a voltage pulse.

187. The method as in any one of claims 81, 84, 102, 103, 104, 105, 106, 109, or 111, 162, 163, 164, wherein said electrical signal is voltage regulated.

188. The method as in any one of claims 81, 84, 102, 103, 104, 105, 106, 109, or 111, 162, 163, 164, wherein said electrical signal comprises a voltage amplitude within the range of 1 microvolt to 1000 volts.

189. The method as in any one of claims 81, 84, 102, 103, 104, 105, 106, 109, or 111, 162, 163, 164, wherein said electrical signal comprises a voltage amplitude within the range of 1 volt to 10 volts.

190. The method as in any one of claims 27, 38, or 49, wherein said energy is activating.

191. The method as in any one of claims 81, 84, 102, 103, 104, 105, 106, 109, or 111, 162, 163, 164, wherein said signal is activating.

192. The method as in any one of claims 27, 38, or 49, wherein said energy is applied to control activity of intermediolateral nucleus.

193. The method as in any one of claims 81, 84, 102, 103, 104, 105, 106, 109, or 111, 162, 163, 164, wherein said signal is applied to control activity of intermediolateral nucleus.

194. The method as in any one of claims 27, 38, or 49, wherein said energy is applied to control body weight.

195. The method as in any one of claims 81, 84, 102, 103, 104, 105, 106, 109, or 111, 162, 163, 164, wherein said signal is applied to control body weight.

196. The method as in any one of claims 27, 38, or 49, wherein said energy is applied to control metabolic rate.

197. The method as in any one of claims 81, 84, 102, 103, 104, 105, 106, 109, or 111, 162, 163, 164, wherein said signal is applied to control metabolic rate.

198. The method as in any one of claims 27, 38, or 49, wherein said energy is applied to control appetite.

199. The method as in any one of claims 81, 84, 102, 103, 104, 105, 106, 109, or 111, 162, 163, 164, wherein said signal is applied to control appetite.

200. The method as in any one of claims 27, 38, or 49, wherein said energy is applied to control satiety.

201. The method as in any one of claims 81, 84, 102, 103, 104, 105, 106, 109, or 111, 162, 163, 164, wherein said signal is applied to control satiety.

202. The method as in any one of claims 27, 38, 49, 81, 84, wherein said treating a user comprises the treatment of obesity.

203. The method as in any one of claims 102, 103, 104, 105, 106, 109, or 111, wherein the method to treat as user comprises the treatment of obesity.

204. The method as in any one of claims 27, 38, or 49, wherein delivery of said energy modulates activity of sympathetic neurons.

205. The method as in any one of claims 81, 84, 102, 103, 104, 105, 106, 109, or 111, 162, 163, 164, wherein delivery of said signal modulates activity of sympathetic neurons.

206. The method as in any one of claims 27, 38, or 49, wherein delivery of said energy increases metabolic rate.

207. The method as in any one of claims 81, 84, 102, 103, 104, 105, 106, 109, or 111, 162, 163, 164, wherein delivery of said signal increases metabolic rate.

208. The method as in any one of claims 27, 38, or 49, wherein delivery of said energy decreases appetite.

209. The method as in any one of claims 81, 84, 102, 103, 104, 105, 106, 109, or 111, 162, 163, 164, wherein delivery of said signal decreases appetite.

210. The method as in any one of claims 27, 38, or 49, wherein delivery of said energy influences body mass index.

211. The method as in any one of claims 81, 84, 102, 103, 104, 105, 106, 109, or 111, 162, 163, 164, wherein delivery of said signal influences body mass index.

212. The method as in any one of claims 27, 38, or 49, wherein delivery of said energy causes a reduction in body fat composition.

213. The method as in any one of claims 81, 84, 102, 103, 104, 105, 106, 109, or 111, 162, 163, 164, wherein delivery of said signal causes a reduction in body fact composition.

214. A method for reducing body weight in a user comprising:
(A) selecting a user of body weight control;
(B) positioning a neuromodulator in communication with at least a component of the intermediolateral nucleus; and
(C) modulating sympathetic activity for control of body weight.

215. The method as in claim 214, wherein positioning a neuromodulator comprises implanting at least one first spinal cord electrode.

216. The method as in claim 215, further comprising implanting at least one second spinal cord electrode.

217. The method as in claim 216, further comprising implanting at least one second pulse generator in communication with at least one second spinal cord electrode.

218. The method as in claim 216, wherein delivering an electrical signal using at least one second spinal cord electrode causes increase in metabolic rate.

219. The method as in claim 216, wherein delivering an electrical signal using at least one second spinal cord electrode causes reduction in appetite.

220. The method as in claim 216, wherein delivering an electrical signal using at least one second spinal cord electrode causes increase in satiety.

221. The method as in claim 216, wherein delivering an electrical signal using at least one second spinal cord electrode causes reduction in body weight.

222. The method as in claim 215, further comprising implanting at least one first pulse generator, in communication with at least one first spinal cord electrode.

223. The method as in claim 215, wherein delivering an electrical signal using at least one first spinal cord electrode causes increase in metabolic rate.

224. The method as in claim 215, wherein delivering an electrical signal using at least one first spinal cord electrode causes reduction in appetite.

225. The method as in claim 215, wherein delivering an electrical signal using at least one first spinal cord electrode causes increase in satiety.

226. The method as in claim 215, wherein delivering an electrical signal using at least one first spinal cord electrode causes reduction in body weight.

227. The method as in claim 214, wherein modulating sympathetic activity causes increase in metabolic rate.

228. The method as in claim 214, wherein modulating sympathetic activity causes reduction in appetite.

229. The method as in claim 214, wherein modulating sympathetic activity causes increase in satiety.

230. The method as in claim 214, wherein modulating sympathetic activity causes reduction in body weight.

231. The method as in any one of claims 27, 38, or 49, wherein delivery of said energy is performed using a spinal cord stimulation electrode.

232. The method as in any one of claims 81, 84, 102, 103, 104, 105, 106, 109, or 111, 162, 163, 164, wherein delivery of said signal is performed using a spinal cord stimulation electrode.

233. The method as in any one of claims 27, 38, or 49, wherein said energy parameters are selected to cause weight reduction.

234. The method as in any one of claims 81, 84, 102, 103, 104, 105, 106, 109, or 111, 162, 163, 164, wherein said signal parameters are selected to cause weight reduction.

* * * * *